US 9,480,457 B2

(12) United States Patent
Kondou

(10) Patent No.: US 9,480,457 B2
(45) Date of Patent: Nov. 1, 2016

(54) ULTRASOUND DIAGNOSTIC DEVICE AND ULTRASOUND IMAGE DISPLAY METHOD

(75) Inventor: Masanao Kondou, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 129 days.

(21) Appl. No.: 14/342,430

(22) PCT Filed: May 30, 2012

(86) PCT No.: PCT/JP2012/063846
§ 371 (c)(1),
(2), (4) Date: Mar. 3, 2014

(87) PCT Pub. No.: WO2013/035393
PCT Pub. Date: Mar. 14, 2013

(65) Prior Publication Data
US 2014/0236001 A1    Aug. 21, 2014

(30) Foreign Application Priority Data
Sep. 8, 2011    (JP) .................. 2011-195954

(51) Int. Cl.
*A61B 8/00* (2006.01)
*A61B 8/08* (2006.01)
(Continued)

(52) U.S. Cl.
CPC .............. *A61B 8/0841* (2013.01); *A61B 8/12* (2013.01); *A61B 8/14* (2013.01); *A61B 8/4254* (2013.01);
(Continued)

(58) Field of Classification Search
USPC ......................................... 600/440
See application file for complete search history.

(56) References Cited

U.S. PATENT DOCUMENTS

2004/0019270 A1    1/2004   Takeuchi
2005/0033160 A1*   2/2005   Yamagata .............. A61B 6/12
                                                 600/425

(Continued)

FOREIGN PATENT DOCUMENTS

JP    A-2006-167267    6/2006
JP    2007-185526 A    7/2007

(Continued)

OTHER PUBLICATIONS

May 5, 2015 Extended Search Report issued in European Patent Application No. 12830733.7.

(Continued)

*Primary Examiner* — Patricia Park
(74) *Attorney, Agent, or Firm* — Oliff PLC

(57) ABSTRACT

An ultrasound image is displayed while clarifying a positional relationship with an ultrasound probe. An ultrasound diagnostic device is provided with an ultrasound probe, a first position detecting means for detecting a position of the ultrasound probe, an ultrasound image generating means for generating an ultrasound image by using a reflected echo signal, an ultrasound volume data generating means for generating three-dimensional ultrasound volume data by accumulating the ultrasound images, a reference image generating means for generating a ultrasound reference image of an arbitrary cross section by using the ultrasound volume data and displaying an ultrasound probe mark indicating the position of the ultrasound probe in a superimposed manner on a position in the ultrasound reference image, the position corresponding to the ultrasound probe position detected by the first position detecting means, and a display means for displaying the ultrasound image and the ultrasound reference image.

12 Claims, 12 Drawing Sheets

(51) Int. Cl.
  *A61B 8/14*   (2006.01)
  *G09G 5/377*  (2006.01)
  *A61B 8/12*   (2006.01)
  *G01S 7/52*   (2006.01)
  *A61B 17/34*  (2006.01)

(52) U.S. Cl.
  CPC .............. *A61B 8/4444* (2013.01); *A61B 8/463* (2013.01); *A61B 8/466* (2013.01); *A61B 8/483* (2013.01); *A61B 8/5207* (2013.01); *A61B 8/5261* (2013.01); *A61B 8/5276* (2013.01); *G09G 5/377* (2013.01); *A61B 8/145* (2013.01); *A61B 8/467* (2013.01); *A61B 8/523* (2013.01); *A61B 2017/3413* (2013.01); *G01S 7/52073* (2013.01); *G01S 7/52074* (2013.01); *G01S 7/52084* (2013.01)

(56) References Cited

U.S. PATENT DOCUMENTS

| | | | |
|---|---|---|---|
| 2005/0090742 A1 | 4/2005 | Mine et al. | |
| 2009/0066727 A1* | 3/2009 | Lu | G01S 7/52046 345/643 |
| 2009/0275833 A1* | 11/2009 | Ikeda | A61B 8/0833 600/443 |
| 2009/0306504 A1 | 12/2009 | Arai et al. | |
| 2010/0171741 A1* | 7/2010 | Brill | A61B 19/5244 345/424 |
| 2010/0174192 A1 | 7/2010 | Azuma | |
| 2010/0222680 A1* | 9/2010 | Hamada | A61B 8/06 600/443 |
| 2010/0286526 A1 | 11/2010 | Okamura et al. | |
| 2011/0125020 A1 | 5/2011 | Kondou | |

FOREIGN PATENT DOCUMENTS

| | | |
|---|---|---|
| JP | 2009-089736 A | 4/2009 |
| JP | A-2009-95371 | 5/2009 |
| JP | A-2010-69018 | 4/2010 |
| JP | 2010-162058 A | 7/2010 |
| WO | WO 2010/007860 A1 | 1/2010 |

OTHER PUBLICATIONS

Jul. 10, 2012 International Prelilminary Report on Patentability issued in International Patent Application No. PCT/JP2012/063846.
International Search Report issued in International Application No. PCT/JP2012/063846 on Jul. 10, 2012 (with translation).

* cited by examiner

ULTRASOUND DIAGNOSTIC DEVICE AND ULTRASOUND IMAGE DISPLAY METHOD

TECHNICAL FIELD

The present invention relates to an ultrasound diagnostic device and an ultrasound image display method, and more particularly, it relates to a technique for displaying an ultrasound image.

BACKGROUND ART

In diagnosis using an ultrasound diagnostic device, an operator such as a doctor scans a diagnosis portion by an ultrasound probe, and this provides an advantage that it is possible to easily obtain a tomographic image of the diagnosis portion in real time. On the other hand, an ultrasound tomographic image (hereinafter, referred to as "ultrasound image") is less easily viewable as morphological information of a whole body of test object, than a tomographic image obtained by a magnetic resonance imaging device (hereinafter, referred to as "MRI device") or an X-ray computed tomography scanner (hereinafter, referred to as "X-ray CT scanner").

Therefore, the patent document 1, for example, discloses an ultrasonic diagnostic device in which a position and a posture of an ultrasound endoscope is detected according to a position detection sensor mounted on the ultrasound endoscope, thereby reconstructing an image of the same cross section as that of an ultrasound image, from volume data of an MRI image or a CT image being taken in advance, this reconstructed image and the ultrasound image are displayed on a monitor, being synchronized with each other.

PRIOR ART DOCUMENT

Patent Document

Patent Document 1: Japanese Unexamined Patent Application Publication No. 2009-095371

DISCLOSURE OF THE INVENTION

Problem To Be Solved By the Invention

The disclosure of the patent document 1 has a problem that though morphological information of the ultrasound image is complemented, positional relationship between the ultrasound image and the ultrasound probe is unclear. Particularly, in the procedure for taking an image by inserting the ultrasound probe into the body cavity of a test object, it is not possible to visually recognize the position of the ultrasound probe, and therefore, the aforementioned problem becomes more obvious.

The present invention has been made in view of the aforementioned problem, and an object of the present invention is to provide an ultrasound diagnostic device and an ultrasound image display method for presenting a positional relationship between the ultrasound probe and a display screen.

Means To Solve the Problem

In order to solve the aforementioned problem, the ultrasound diagnostic device relating to the present invention is provided with an ultrasound probe for emitting an ultrasound wave and receiving a reflected wave of the ultrasound wave, a first position detecting means for detecting a position of the ultrasound probe, an ultrasound image generating means for generating an ultrasound image by using a reflected echo signal based on the reflected wave, a reference image generating means for generating a reference image of an arbitrary cross section by using three-dimensional volume data of a test object and displaying an ultrasound probe mark indicating the position of the ultrasound probe being detected in a superimposed manner on the reference image, and a display means for displaying the ultrasound image and the reference image.

In addition, an ultrasound image display method is provided, including a step of generating a reference image of an arbitrary cross section by using three-dimensional volume data of a test object, a step of displaying an ultrasound probe mark indicating a position of the ultrasound probe in a superimposed manner on the reference image, and a step of displaying the ultrasound image based on the reflected wave received from the ultrasound probe and the reference image.

Effect of the Invention

According to the present invention, a reference image on which an ultrasound probe mark is displayed in a superimposed manner is displayed, thereby providing an ultrasound diagnostic device and an ultrasound image display method that are able to present a positional relationship between the ultrasound probe and the display screen.

BRIEF DESCRIPTION OF DRAWINGS

FIG. 3(a) illustrates a positional relationship between the ultrasound emitting surface and the ultrasound image based on the ultrasound wave emitted therefrom, and FIG. 3(b) illustrates each of the reference images and their positional relationship;

FIG. 5(a) illustrates operation of the trackball and screen transition along therewith, and FIG. 5(b) illustrates shifting of the position of the third reference image and the mark indicating the position, along with the operation of the track ball;

FIG. 6(a) illustrates operation of the track ball and screen transition along therewith, and FIG. 6(b) illustrates shifting of the position of the third reference image and the mark indicating the position, along with the operation of the track ball;

when the track ball is rotated to the right; FIG. 7(a) illustrates operation of the trackball and screen transition along therewith, and FIG. 7(b) illustrates shifting of the position of the second reference image and the mark indicating the position, along with the operation of the track ball;

FIG. 8(a) illustrates the screen transition including the third reference image, and FIG. 8(b) illustrates shifting of the position of the third reference image;

FIG. 9(a) indicates the operating directions of the track ball, and FIG. 9(b) illustrates the third reference image after the movement in association with each operating direction;

FIG. 10(a) illustrates the rotating directions of the second reference image and operating directions of the track ball, and FIG. 10(b) illustrates the second reference image after the rotation;

BEST MODE FOR CARRYING OUT THE INVENTION

Hereinafter, preferred embodiments of the present invention will be explained with reference to the drawings. It is to be noted that in the following description, a constituent having the same function will be labeled the same, and tedious explanation will not be made.

Figure 1:
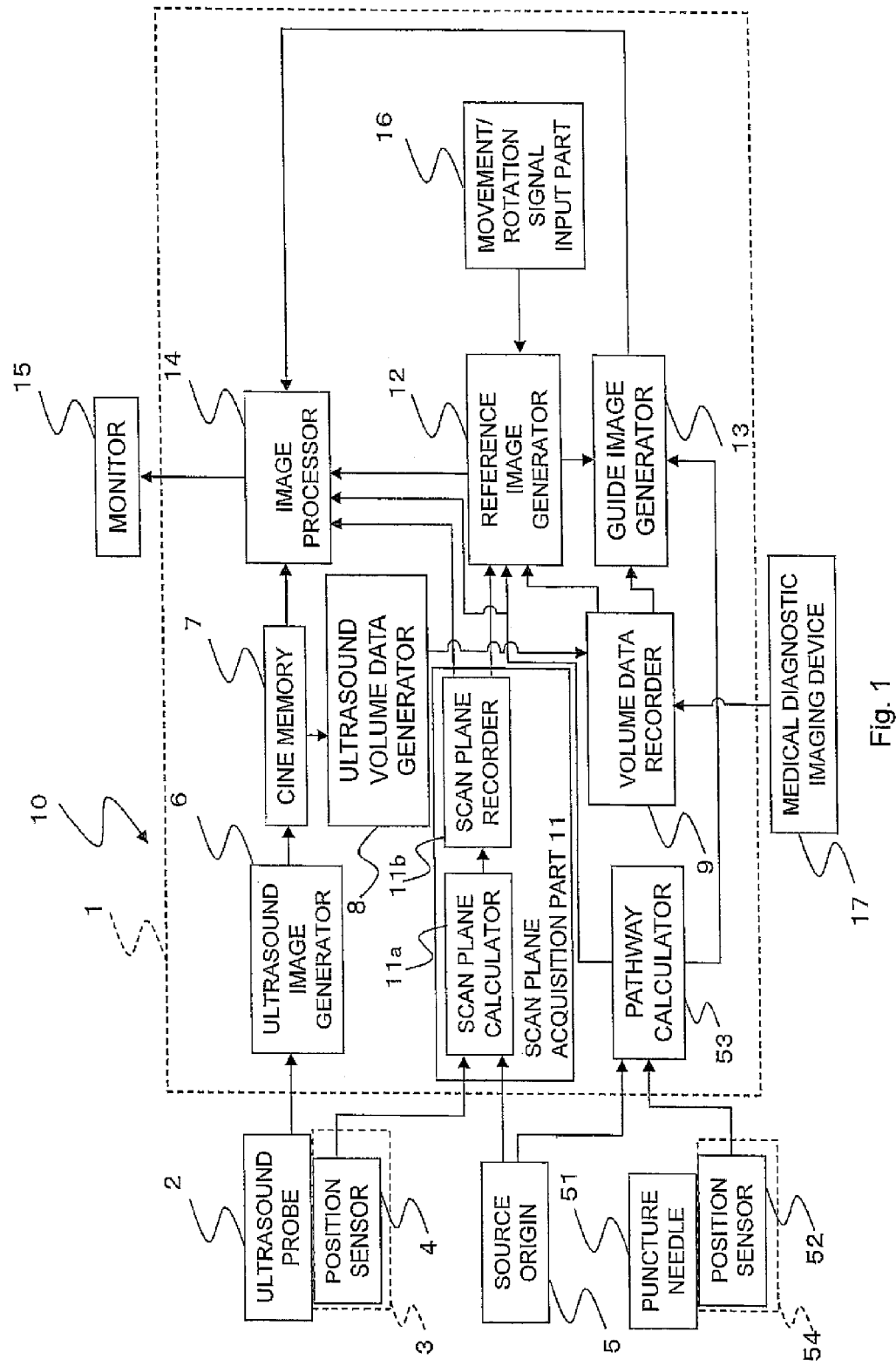
FIG. 1 is a diagram schematically illustrating an overall configuration of the ultrasound diagnostic device.

Firstly, with reference to FIG. 1, an explanation will be made as to a schematic configuration of the ultrasound diagnostic device relating to the embodiments of the present invention. FIG. 1 is a diagram illustrating an overall schematic configuration of the ultrasound diagnostic device relating to the embodiments of the present invention. The ultrasound diagnostic device 10 incorporates as primary parts, an ultrasound diagnostic device main unit 1, an ultrasound probe 2, a position sensor 4, a source origin 5, and a monitor 15. The ultrasound diagnostic device main unit 1 is roughly divided into a system for generating an ultrasound image, and a system for generating a reference image used for reference upon performing a diagnosis on the ultrasound image. The system for generating the ultrasound image includes, an ultrasound image generator 6 for generating an ultrasound image based on a reflected echo signal from the ultrasound probe 2, a cine memory 7 for temporarily storing multiple ultrasound images, and an ultrasound volume data generator 8 for generating three-dimensional ultrasound volume data based on the multiple ultrasound images. The system for generating the reference image is provided with a volume data recorder 9 for storing the three-dimensional volume data taken by a medical diagnostic imaging device 17 such as an MRI device, a CT scanner, and other ultrasound diagnostic device, for instance, a scan plane acquisition part 11 for detecting a position and a posture of the ultrasound probe 2, based on signals of the position sensor 4 and the source origin 5, a reference image generator 12 for generating a reference image based on the three-dimensional volume data and the ultrasound volume data of a test object stored in the volume data recorder 9, the reference image being used for reference upon performing a diagnosis on the ultrasound image, a guide image generator 13 for generating a guide image indicating a cross section position of the reference image, and a movement/rotation signal input part 16 for accepting inputs of a movement/rotation type, a moving amount/rotating amount, and a moving direction/rotating direction of the reference image. In addition, the ultrasound diagnostic device main unit 1 includes an image processor 14 for performing a display process, establishing association between the ultrasound image and the cross section position of the reference image.

In addition, the ultrasound diagnostic device main body 1 is provided with a pathway calculator 53. This pathway calculator 53 is to calculate an entry pathway of a puncture needle 51. It is further possible that the current position and inclination of the puncture needle 51 are calculated, based on an output signal from a position sensor 52 that is fixed on the puncture needle 51 via a position sensor fixation mechanism 54 and an output signal from the source origin 5, and then an extension of the core line of the puncture needle 51 is obtained as the entry pathway. The puncture needle 51, the position sensor 52, the pathway calculator 53, and the position sensor fixation mechanism 54 are used in the second embodiment.

Though not illustrated, it is to be noted that the ultrasound diagnostic device main unit 1 is equipped with an interface for inputting the three-dimensional volume data of the test object imaged by a medical diagnostic imaging device 17, ultrasound volume data imaged by other ultrasound diagnostic device, and the like. Then, the ultrasound diagnostic device main unit 1 is directly connected to the medical diagnostic imaging device 17 via the interface, receives the three-dimensional volume data, and stores the volume data in the volume data recorder 9. It is further possible to store the three-dimensional volume data in the volume data recorder 9 within the ultrasound diagnostic device main unit, via a network or via a portable recording medium, such as a USB memory. Hereinafter, each constitutional element will be explained in detail.

The ultrasound probe 2 transfers an ultrasound wave from the ultrasound emitting surface, also receives a reflected wave of the ultrasound wave, and outputs a reflected echo signal to the ultrasound image generator 6.

The ultrasound image generator 6 generates an ultrasound image for one frame, at each position in the moving direction of the ultrasound probe 2 (the moving direction corresponds to an inserting direction, if the ultrasound probe 2 is a type to be inserted into a body cavity). Then, along with shifting the position of the ultrasound probe 2, the ultrasound image generator generates ultrasound images associated with multiple frames, at multiple positions. The cine memory 7 temporarily stores the ultrasound images for the multiple frames. The ultrasound volume data generator 8 generates three-dimensional ultrasound volume data that is obtained by accumulating the ultrasound images of the multiple frames along one direction (the moving direction of the ultrasound probe 2), based on the ultrasound images temporarily stored in the cine memory 7. The volume data recorder 9 records the three-dimensional ultrasound volume data thus generated, and also records the three-dimensional volume data imaged by the medical diagnostic imaging device 17.

The position sensor 4 such as a magnetic sensor for detecting the position and posture of the ultrasound probe 2 is fixed on the ultrasound probe 2 via the position sensor fixation mechanism 3 that is mounted on the ultrasound probe 2. In addition, the source origin 5 for generating source such as magnetic field in the coordinate system including the test object, is arranged on the side of the bed on which the test object is laid, for instance. The position sensor 4 and the source origin 5 are electrically connected to the scan plane acquisition part 11, and signals from the position sensor 4 and the source origin 5 are outputted to the scan plane acquisition part 11.

The scan plane acquisition part 11 is provided with a scan plane calculator 11a for acquiring positional information such as the position and inclination angle of the ultrasound probe 2 based on the signals outputted from the position sensor 4 and the source origin 5, calculates the three-dimensional position, inclination angle, and the like, of the ultrasound probe 2, so as to obtain the coordinates of the scan plane (the cross section of the ultrasound image) of the ultrasound probe 2, and a scan plane recorder 11b for recording the coordinates of the scan plane being obtained. In the present embodiment, the position detecting by using the magnetic field is taken as an example for detecting the position of the ultrasound probe 2. However, this is not the only example, and it is possible to employ a different position detecting method being publicly known. The coordinates of the scan plane being obtained are outputted to the reference image generator 12 and the image processor 14.

The reference image generator 12 uses the coordinates obtained by the scan plane acquisition part 11, so as to generate from the volume data recorded in the volume data recorder 9, a reference image having the same cross section as that of the ultrasound image (hereinafter, referred to as "the first reference image"), a reference image that is obtained by rotating the first reference image by 90° or 270°, assuming the depth direction thereof as a rotation axis (hereinafter, referred to as "the second reference image"), a reference image being parallel to the ultrasound emitting surface of the ultrasound probe 2 (hereinafter, referred to as "the third reference image"), and further a reference image of an optional cross section. The reference image generator 12 further subjects each of the reference images being generated to a processing such as showing a dotted line indicating the position of another reference image in such a manner as superimposed thereon, or hiding the dotted line.

The reference image generator 12 calculates the coordinates of the ultrasound emission area (also referred to as "FOV") within the ultrasound image based on the scan plane coordinates, and performs processing such as reducing brightness of the region other than the ultrasound emission area, on the first, the second, and the third reference images, or hiding the region other than the ultrasound emission area.

Furthermore, the reference image generator 12 changes the image size and the frame rate of the reference image according to the movement of the ultrasound probe 2, thereby varying the speed for reconstructing the reference image. In other words, if the ultrasound probe 2 moves quickly in the moving direction, a higher priority is placed on the frame rate than the image quality, and the reference image is depicted at high speed. On the other hand, if the ultrasound probe 2 moves slowly, a higher priority is placed on the image quality than the frame rate in reconstructing and depicting the reference image. This allows the reference image to be displayed, following the movement of the ultrasound probe 2.

The reference image generator 12 outputs to the image processor 14, the positional information indicating the cross section position of each reference image and the reference image being generated. The positional information indicating the cross section position of each reference image is also outputted to the guide image generator 13. In other words, the reference image generating means (the reference image generator 12) generates multiple reference images made up of different cross sections, displays a mark indicating a slice pitch of another reference image in a superimposed manner on one reference image, and highlights the mark indicating the slice pitch that shows the cross section position of another reference image being displayed on the display means (monitor 15).

Furthermore, a first image processing means (guide image generator 13) is provided for displaying the mark indicating the slice pitch of the reference image in a superimposed manner on the ultrasound image, and highlighting the mark indicating the slice pitch that shows the cross section position of the reference image displayed on the display means (monitor 15).

The guide image generator 13 uses the three-dimensional volume data recorded in the volume data recorder 9, and the cross-section positional information of the reference image obtained from the reference image generator 12, so as to generate a guide image being displayed in such a manner that the cross section of the reference image in semitransparent color is superimposed on the three-dimensional visible image of the test object. As a method for generating the three-dimensional image of the test object, to be used for the guide image, a well-known method may be applied, for example, volume rendering, surface rendering, and the like. The guide image being generated is outputted to the image processor 14.

An association between the three-dimensional volume data of the test object acquired by the medical diagnostic imaging device 17 and the position of the ultrasound probe 2 is established by applying a well-known method, such as displaying on the monitor 15, a test object image made up of the three-dimensional volume data of the test object and the ultrasound image obtained by the ultrasound probe 2, and allowing an operator to designate by a pointing device, a characteristic portion included in the test object image and the same characteristic portion included in the ultrasound image. In addition, the ultrasound image is memorized in association with the positional information thereof in the moving direction, at the time when the ultrasound image is acquired.

The image processor 14 is connected to the scan plane acquisition part 11, the cine memory 7, the reference image generator 12, and the guide image generator 13. Then, an ultrasound image is acquired from the cine memory 7, a reference image is acquired from the reference image generator 12, and a guide image is acquired from the guide image generator 13. Then, the coordinates of the scan plane calculated by the scan plane acquisition part 11 and the cross-section positional information of the reference image are used to perform processing for superimposing/hiding the dotted line indicating the position of the reference image on the ultrasound image. Furthermore, the image processor performs a processing for establishing an association among the positions of the ultrasound image, the reference image, and the guide image, so as to display those images on the monitor 15.

By way of example, the ultrasound image and the reference image may be displayed side by side, or the reference image may be rendered semi-transparent and displayed on the ultrasound image in such a manner as superimposed thereon. If it is superimposed thereon, only one image enables easy comparison between the ultrasound image and the reference image. It is further possible that an image in the cine memory 7, an image generated by the reference image generator 12, and an image generated by the guide image generator 13 are combined appropriately and displayed.

In addition, the image processor 14 performs image processing for superimposing the scan plane in semi-transparent color on the guide image. Accordingly, the operator is allowed to grasp the positional relationship three-dimensionally, between the test object and the scan plane of the ultrasound probe 2. It is to be noted that in the present embodiment, the position of the first reference image agrees with the position of the scan plane of the ultrasound image. Therefore, in the following, an explanation will be made, taking as an example that the position of the first reference image is displayed on the guide image. However, "the first reference image" may be read as the scan plane of the ultrasound image.

In the second embodiment described below, the image processor 14 is also connected to the pathway calculator 53, and it is possible to display the pathway and position of the puncture needle 51 acquired from the pathway calculator 53, or the position of the extension of the needle core line may be displayed in a superimposed manner on the ultrasound image.

The movement/rotation signal input part 16 is connected to input units including a pointing device such as a mouse and a track ball, and a keyboard, etc. Then, when the operator manipulates those input units to enter a type selection either movement or rotation, a selection either moving direction or rotating direction, and further a moving amount and a rotating angle. Then, the movement/rotation signal input part 16 acquires those inputted values, and outputs them to the reference image generator 12. The movement/rotation signal input part 16 may also accept an input for selecting an image targeted for moving or rotating.

The reference image generator 12 moves or rotates the reference image according to the inputted values, and the guide image generator 13 shifts the position of the reference image on the guide image. Following this movement, the image processor 14 shifts a mark indicating the reference image being superimposed on the ultrasound image.

Alternatively, when the position of the reference image that is superimposed on the guide image or the position of the reference image that is superimposed on the ultrasound image is moved and/or rotated by using the operating unit including pointing devices, such as the mouse and the trackball, the movement/rotation signal input part 16 detects the moving amount and the rotating amount, and the reference image generator 12 generates a new reference image according to the inputted values being detected, and the reference image on the monitor 15 is also updated and displayed.

Furthermore, the ultrasound diagnostic device 10 is provided with an operation input unit for zooming in and out on an observation site. Upon zooming in and out on the observation site, a display magnification of the observation site is changed in the ultrasound image that is generated by the ultrasound image generator 6. Following this change, the reference image generator 12 changes the display magnification of the reference image (or generates a new reference image) so as to coincide with the new display magnification of the ultrasound image. The ultrasound image or the reference image whose display magnification has been changed is updated and displayed on the monitor 15.

Figure 2:
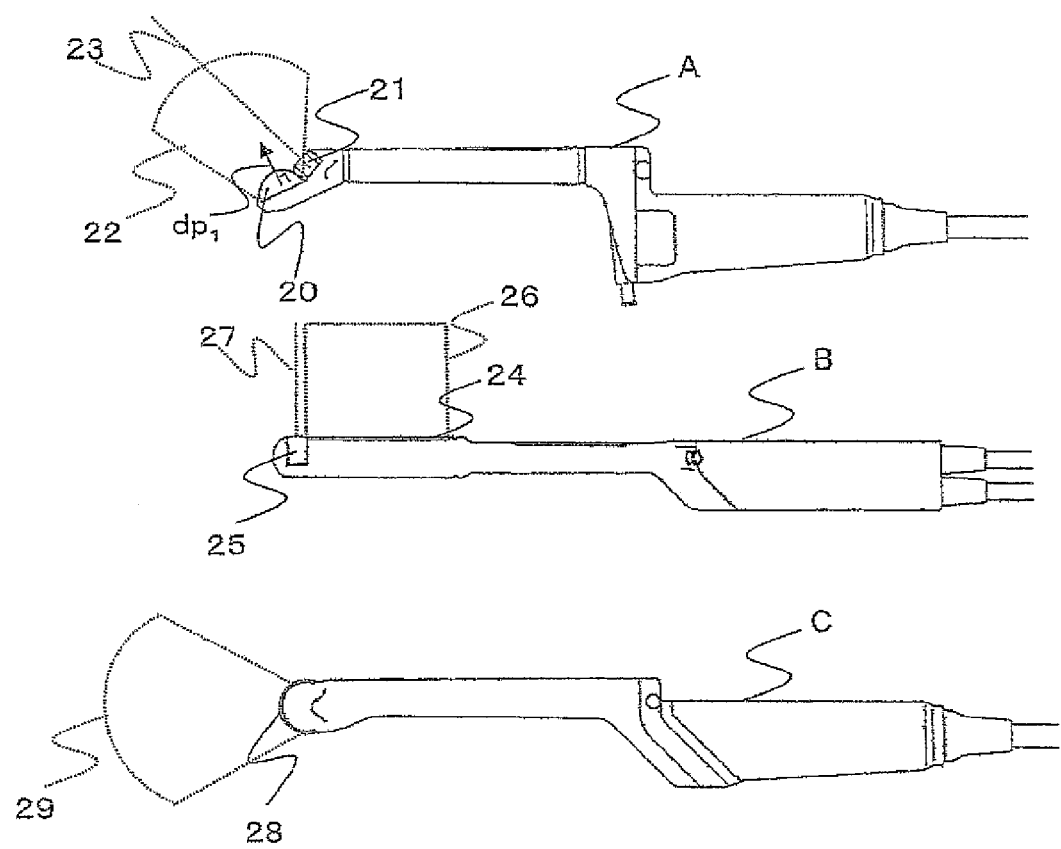
FIG. 2 illustrates a schematic configuration of the ultrasound probe 2.

Next, with reference to FIG. 2, the ultrasound probe 2 will be explained. FIG. 2 illustrates a schematic configuration of the ultrasound probe 2.

As the ultrasound probe 2, it is possible to employ a biplane-type ultrasound probe A for acquiring two ultrasound images simultaneously from two ultrasound emitting surfaces, a non-biplane type ultrasound probe B for acquiring one ultrasound image by switching two ultrasound emitting surfaces, and an ultrasound probe C provided with one ultrasound emitting surface.

The ultrasound probe A is inserted into a body cavity of the test object, including a prostatic region, and sends and receives ultrasound waves within the body cavity. The ultrasound probe A is provided with two ultrasound emitting surfaces 20 and 21. The ultrasound emitting surface 20 is mounted on the tip of the ultrasound probe A. Then, the depth direction dp1 of the ultrasound wave emitted from the ultrasound emitting surface 20 is vertical to the ultrasound emitting surface 20. An image taken by the ultrasound wave emitted from the ultrasound emitting surface 20 corresponds to the first cross-section image 22. The ultrasound emitting surface 21 is provided closer to the center of the ultrasound probe A than the ultrasound emitting surface 20. The depth direction of the ultrasound wave emitted from the ultrasound emitting surface 21 is vertical to the ultrasound emitting surface 21. An image taken by the ultrasound wave emitted from the ultrasound emitting surface 21 corresponds to the second cross-section image 23.

The ultrasound probe B is provided with two ultrasound emitting surfaces 24 and 25, and it is a non-biplane type ultrasound probe that acquires an ultrasound image from either one of the ultrasound emitting surfaces, by switching between the ultrasound emitting surfaces 24 and 25. An image obtained from the ultrasound emitting surface 24 corresponds to the third cross-section image 26, and an image obtained from the ultrasound emitting surface 25 corresponds to the fourth cross-section image 27. The depth directions of the ultrasound emitting surfaces 24 and 25 are vertical to the respective ultrasound emitting surfaces.

The ultrasound probe C is an ultrasound probe that is provided with one ultrasound emitting surface 28. An image obtained from the ultrasound emitting surface 28 corresponds to the fifth cross-section image 29.

The ultrasound probe 2 used in the present embodiments may be any of the ultrasound probes A, B, and C. The present invention may be applied not only to the probe that is to be inserted into the body cavity of the test object, but also to an ultrasound probe for sending and receiving ultrasound waves between the body surface and the internal body, such as a probe used for an abdomen echo.

First Embodiment

The ultrasound diagnostic device 10 of the first embodiment displays reference images on three cross sections being orthogonal to one another, and a guide image in which cross section positions of those reference images are displayed in superimposed manner on the three-dimensional test object image, and further displays a mark indicating the position of the ultrasound probe 2 in a superimposed manner on the reference images.

More specifically, in the first embodiment, according to the three-dimensional volume data recorded in the volume data recorder 9, the following reference images are generated; the first reference image made up of an image of the same cross section as that of the ultrasound image, the second reference image made up of an image of the cross section that is obtained by rotating the first reference image by 90° or by 270° around the depth direction of the ultrasound wave, and the third reference image made up of an image of the surface being parallel to the ultrasound emitting surface, and simultaneously, the mark indicating the position of the ultrasound probe is displayed in superimposed manner on those reference images.

As described above, in the present embodiment, an explanation will be made taking an example that there are displayed reference images, one having the same cross section as that of the ultrasound image and biaxial cross sections orthogonal to the cross section of the ultrasound image. However, the cross sections of the reference images are not limited to those triaxial cross sections, but any cross sections obtained by moving and/or rotating those triaxial cross sections to arbitrary positions may be applicable. In the present embodiment, the reference images are generated based on the ultrasound volume data, but it is alternatively possible to generate the reference images based on the three-dimensional data obtained by an MRI apparatus or an X-ray CT scanner, being recorded in the volume data recorder 9.

Figure 3:
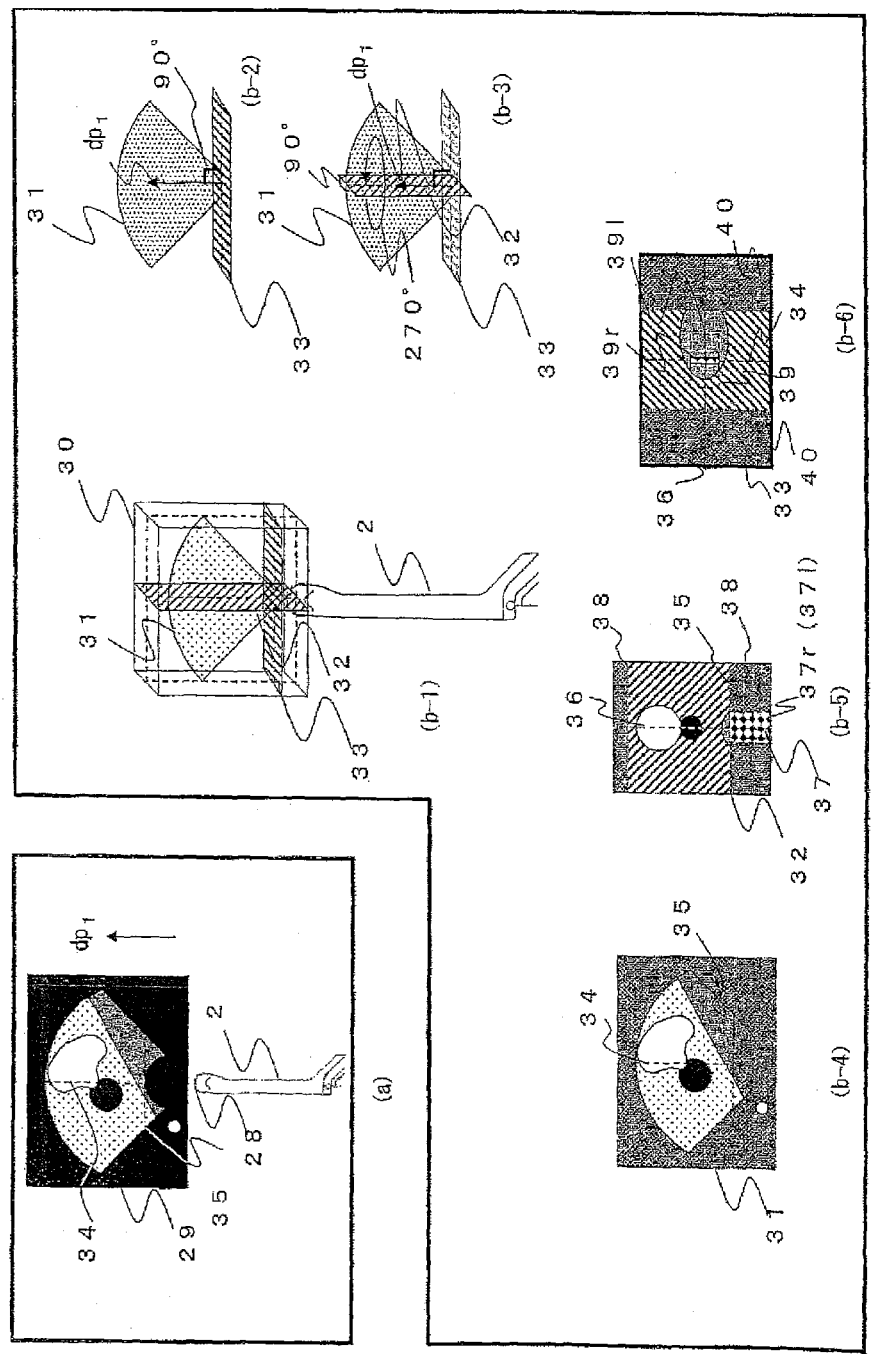
FIG. 3 illustrates a positional relationship between an ultrasound emitting surface and an ultrasound image, and a positional relationship among the first reference image, the second reference image, and the third reference image.
Figure 4:
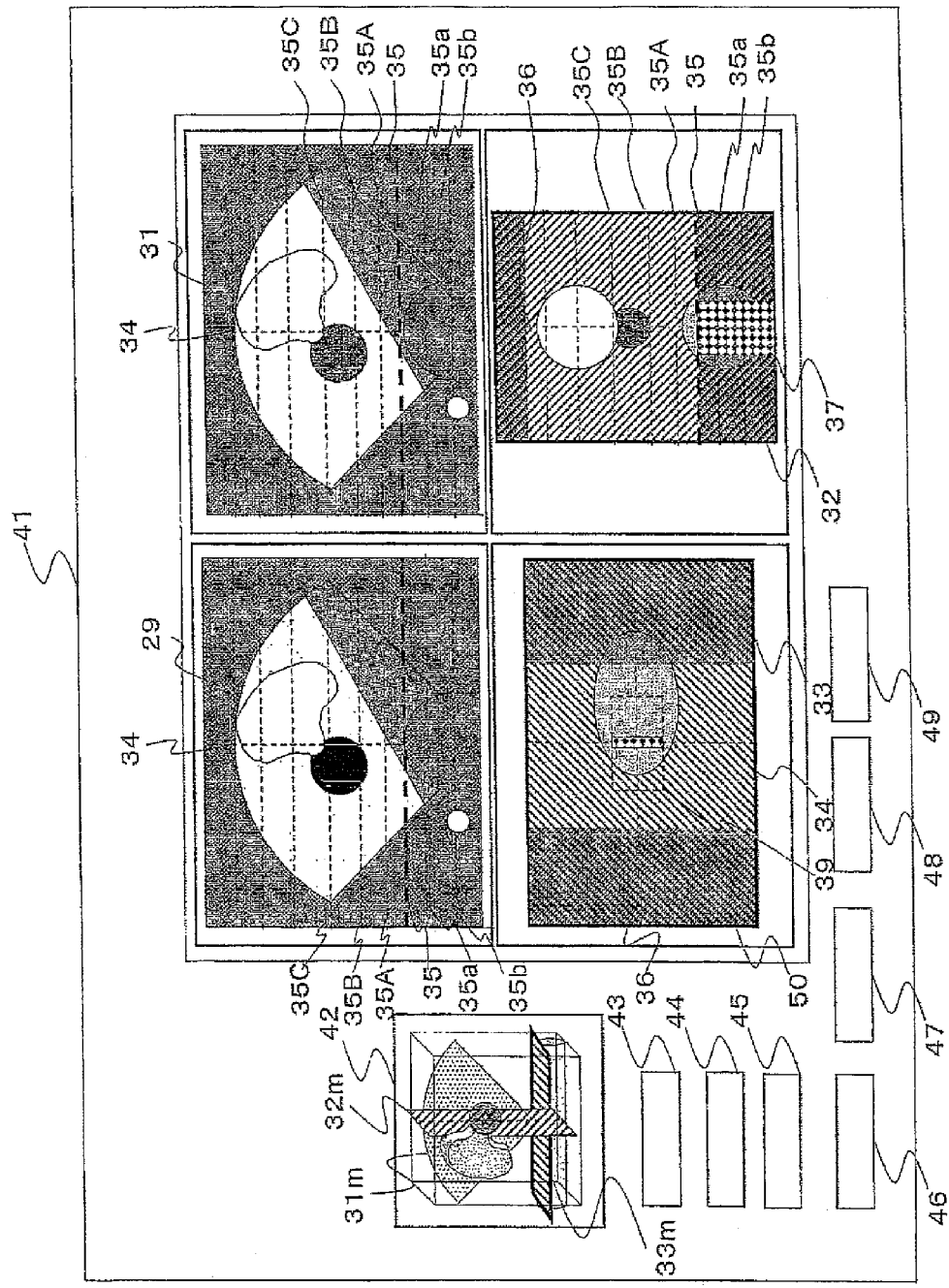
FIG. 4 illustrates a screen display example of the first embodiment.

Hereinafter, with reference to the figures from FIG. 3 to FIG. 7, the first embodiment will be explained. FIG. 3 illustrates the positional relationship between the ultrasound emitting surface and the ultrasound image, and also the positional relationship with the first reference image, the second reference image, and the third reference image; FIG. 3(a) illustrates a positional relationship between the ultrasound emitting surface and the ultrasound image based on the ultrasound wave emitted therefrom, and FIG. 3(b) illustrates the reference images and a positional relationship thereof. FIG. 4 illustrates a screen display example of the first embodiment.

Figure 5:
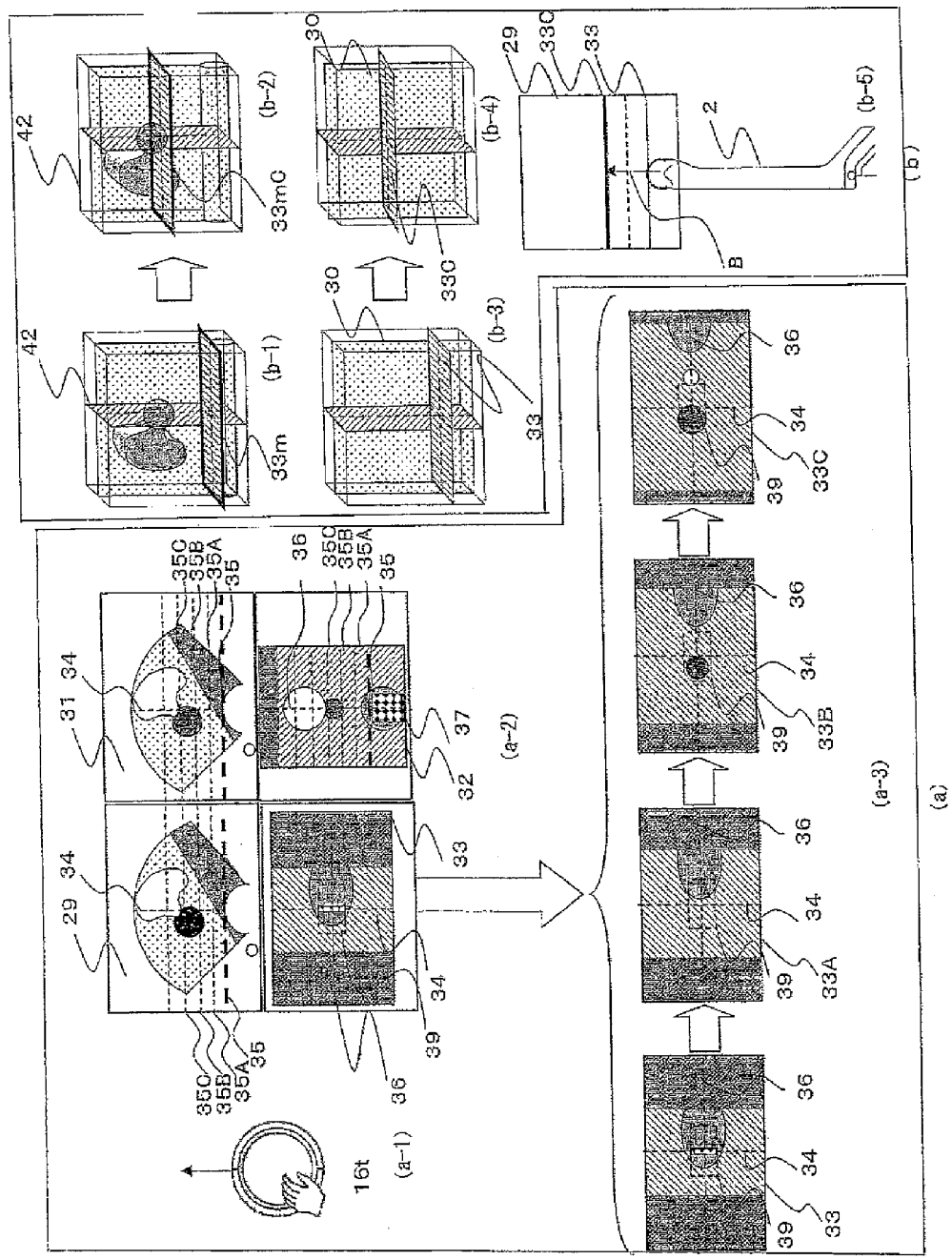
FIG. 5 illustrates a concept that in the state where the third reference image is selected, the third reference image is sequentially switched in the depth direction when the trackball is rotated upwardly.
Figure 6:
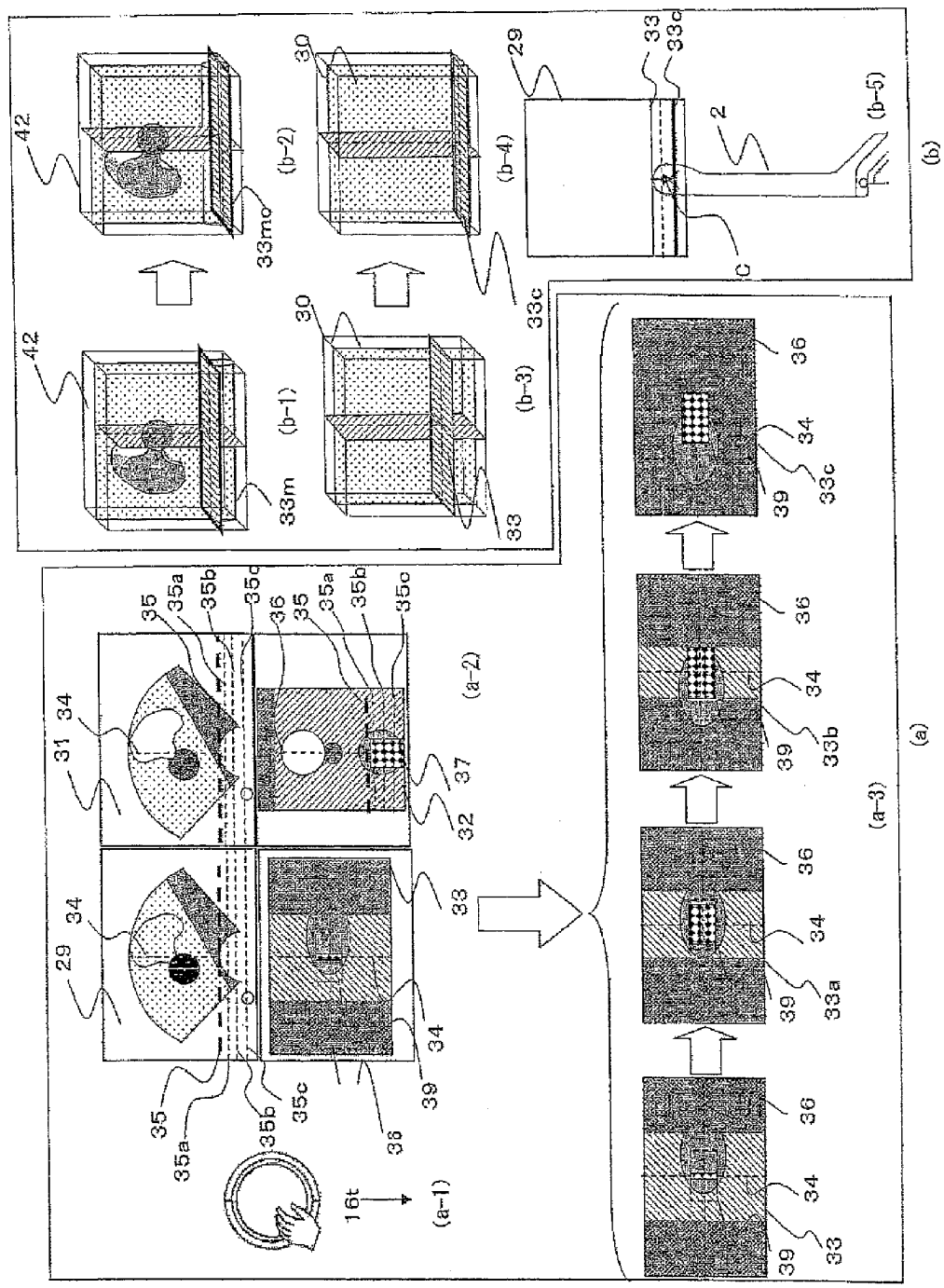
FIG. 6 illustrates a concept that in the state that the third reference image is selected, the third reference image is sequentially switched in the opposite direction of the depth direction when the track ball is rotated downwardly.

FIG. 5 illustrates a concept that the third reference image is sequentially switched in the depth direction when the track ball is rotated upwardly in the state where the third reference image is selected; FIG. 5(a) illustrates operation of the track ball and screen transition along therewith, and FIG. 5(b) illustrates shifting of the position of the third reference image and the mark indicating the position, along with the operation of the track ball. FIG. 6 illustrates a concept that the third reference image is sequentially switched in the opposite direction of the depth direction when the track ball is rotated downwardly in the state that the third reference image is selected; FIG. 6(a) illustrates operation of the track ball and screen transition along therewith, and FIG. 6(b) illustrates shifting of the position of the third reference image and the mark indicating the position, along with the operation of the track ball.

Figure 7:
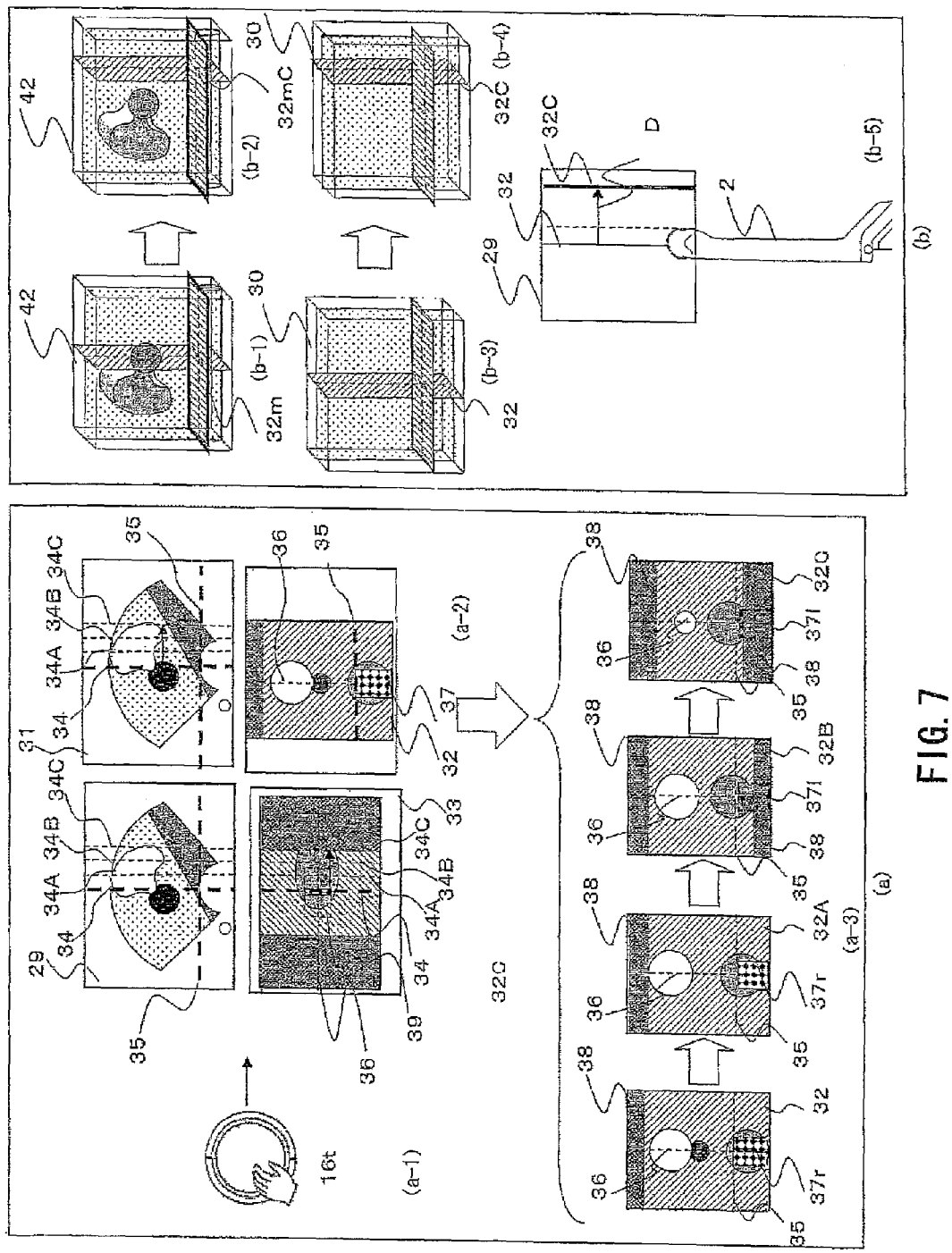
FIG. 7 illustrates a concept that in the state that the second reference image is selected, the second reference image is sequentially switched in the direction orthogonal to the depth direction (the right direction on the paper of FIG. 7)
Figure 8:
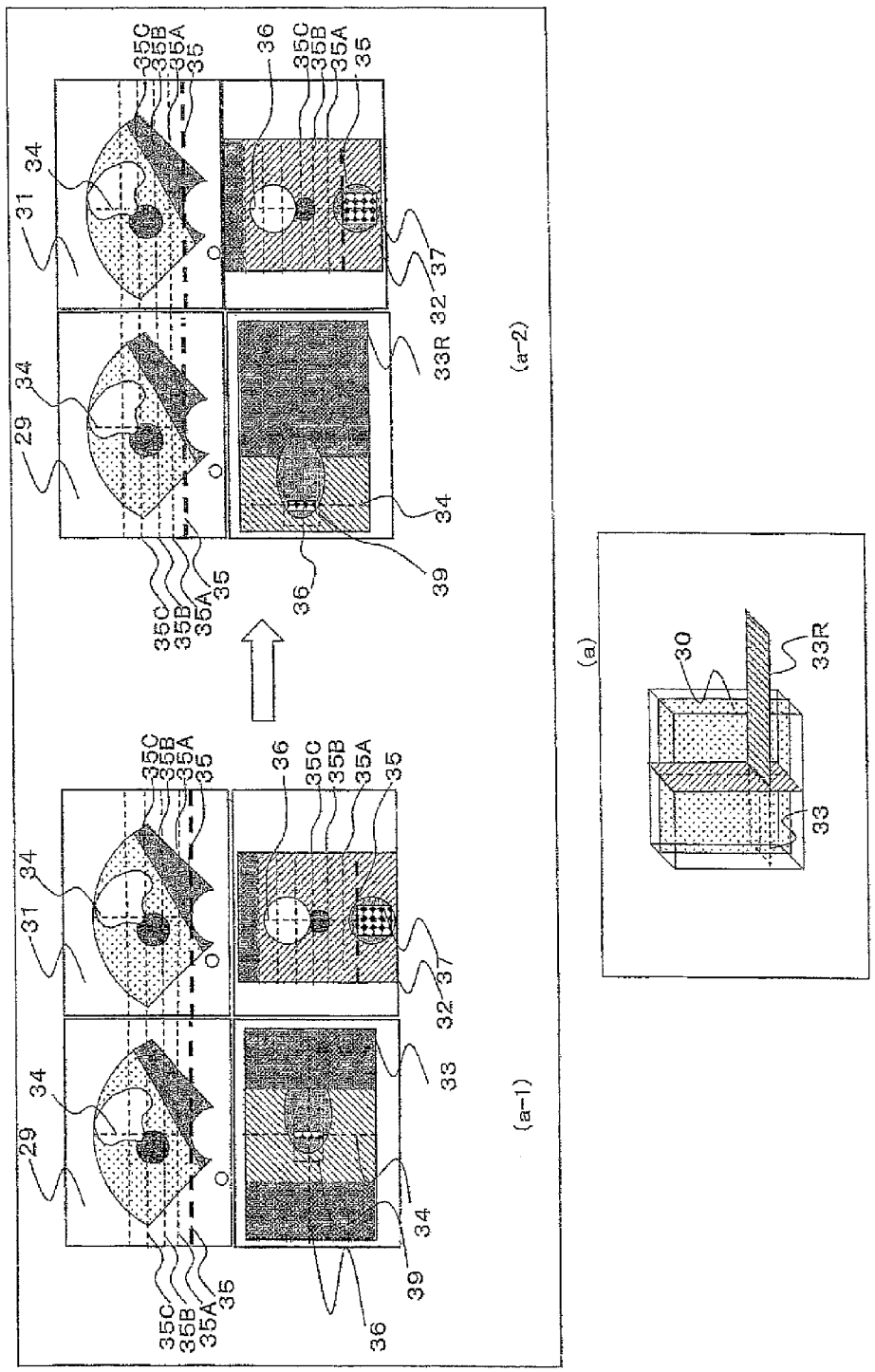
FIG. 8 illustrates screen transition when the track ball is rotated to the right in the state that the third reference image is selected.

FIG. 7 illustrates a concept that the second reference image is sequentially switched in the direction orthogonal to the depth direction (the right direction of FIG. 7 on the paper) when the track ball is rotated to the right, in the state that the second reference image is selected; FIG. 7(a) illustrates operation of the track ball and screen transition along therewith, and FIG. 7(b) illustrates shifting of the position of the second reference image and the mark indicating the position, along with the operation of the track ball. FIG. 8 illustrates screen transition when the track ball is rotated to the right in the state that the third reference image is selected; FIG. 8(a) illustrates the screen transition including the third reference image, and FIG. 8(b) illustrates shifting of the position of the third reference image.

Figure 9:
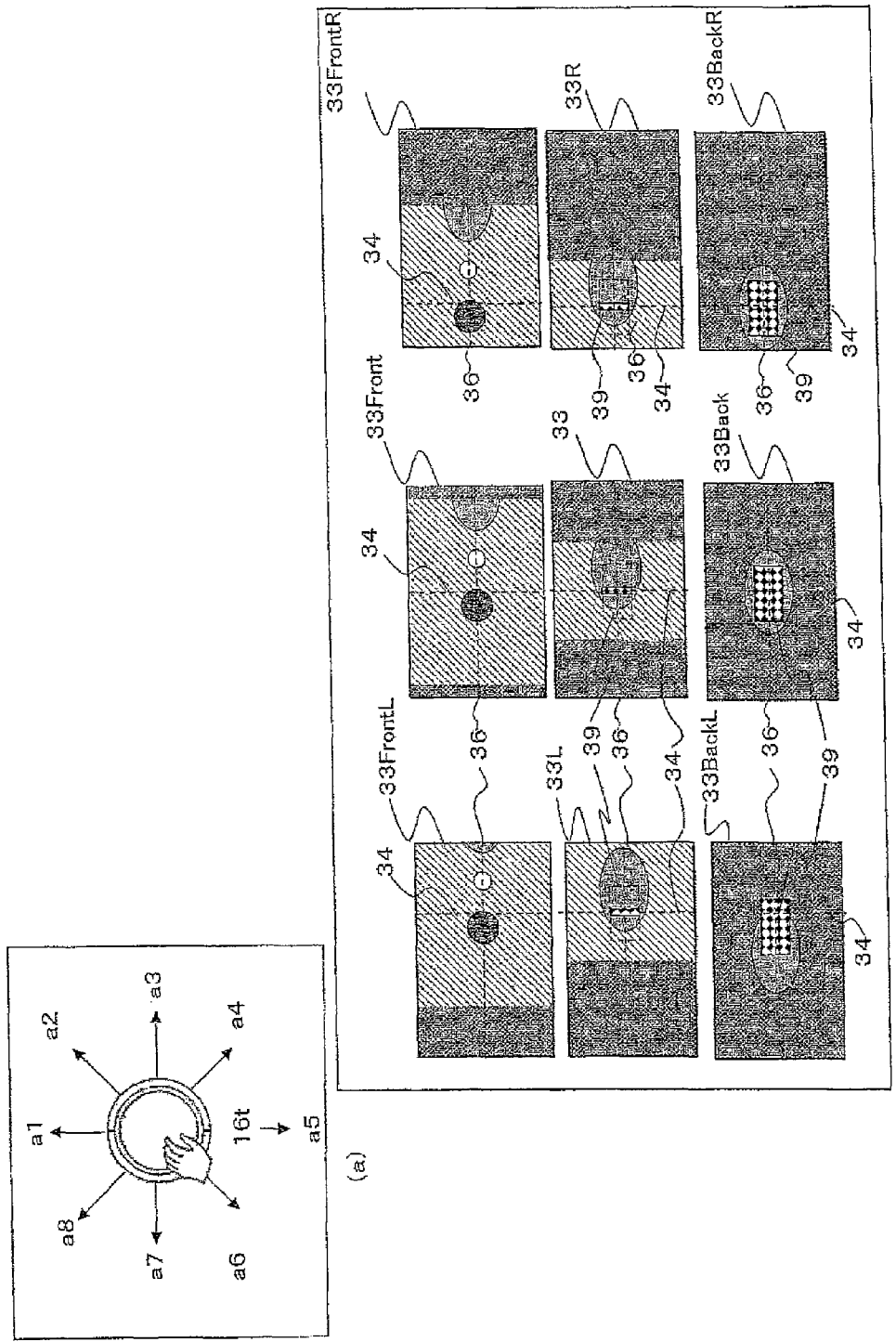
FIG. 9 illustrates the state that the third reference image is moved in multiple directions within the ultrasound emitting surface.
Figure 10:
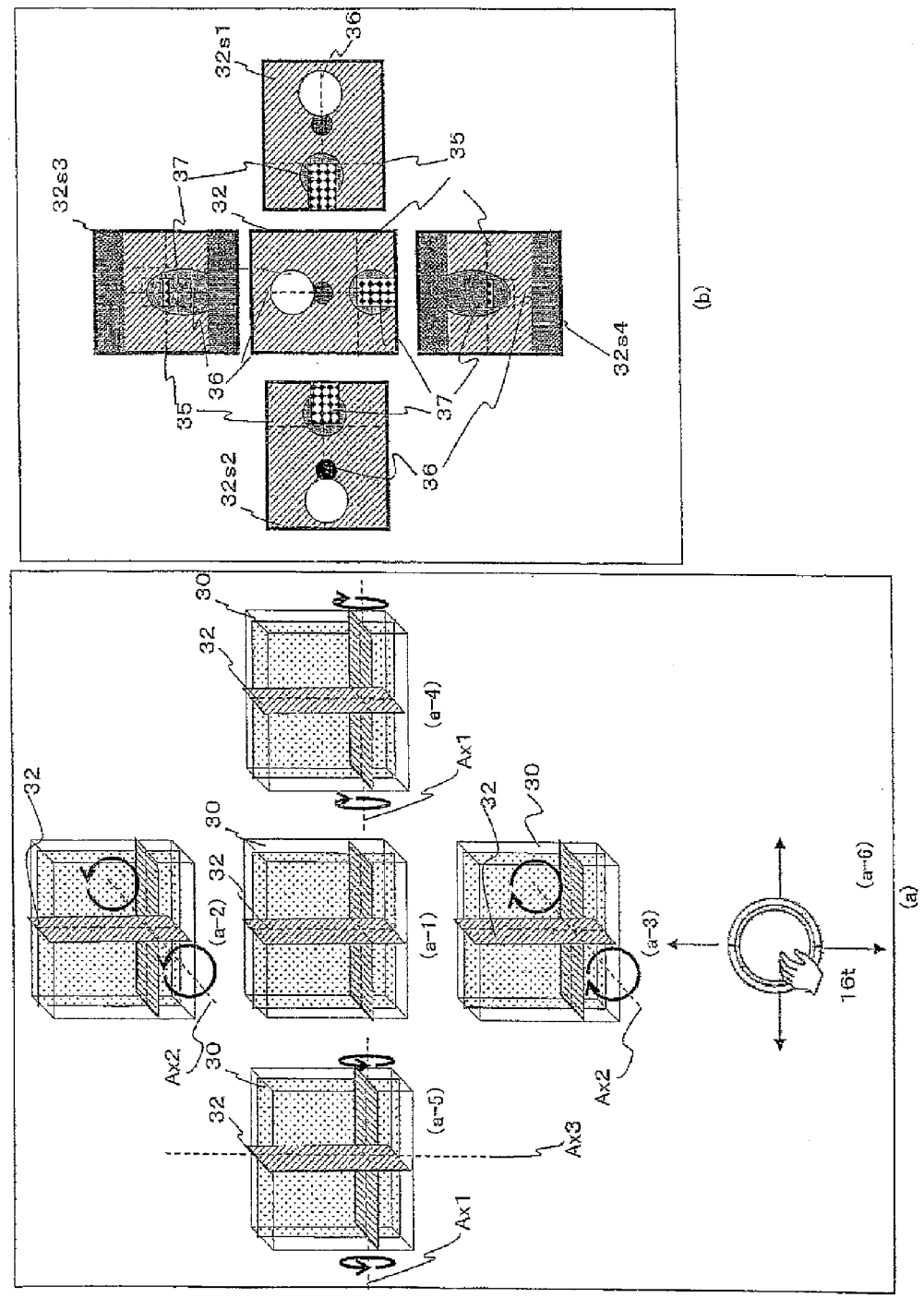
FIG. 10 illustrates the second reference image in the state where it is selected and the rotating direction is set to be "backward, forward, left, and right" by the rotating direction switching button 49, the second reference image being displayed when the track ball 16t is rotated upwardly, downwardly, and to the left and right.

FIG. 9 illustrates the state that the third reference image is moved in multiple directions within the ultrasound emitting surface; FIG. 9(a) indicates the operating directions of the track ball, and FIG. 9(b) illustrates the third reference image after the movement associated with each operating direction. FIG. 10 illustrates the second reference image that is displayed when the track ball 16t is rotated upwardly/downwardly and to the left/right, while the rotating direction is set to the "backward, forward, left, and right" by the rotating direction switching button 49, in the state where the second reference image is selected; FIG. 10(a) illustrates the rotating directions of the second reference image and the operating directions of the track ball, and FIG. 10(b) illustrates the second reference image after the rotation.

Firstly, positional relationships among the ultrasound emitting surface and the ultrasound image, the first reference image, the second reference image, and the third reference image, will be explained. In the following explanation, the ultrasound probe C as shown in FIG. 2 is employed as the ultrasound probe 2. The same explanation is applied to the ultrasound image acquired from the ultrasound emitting surface of the ultrasound probe A or B.

As shown in FIG. 3(a), the ultrasound image 29 generated from the ultrasound wave emitted from the ultrasound emitting surface 28 provided on the tip of the ultrasound prove C corresponds to a region having a substantially fan-like shape expanding toward the depth direction dp1.

In the three-dimensional volume data 30 shown in (b-1) in FIG. 3(b), an image extracted from the same cross section as that of the ultrasound image 29 is referred to as the first reference image 31. The first reference image 31 is orthogonal to the third reference image 33 which is parallel to the ultrasound emitting surface 28 being described below (see FIG. 3(b) (b-2)).

An image obtained by rotating the first reference image 31 by 90° or 270°, assuming the depth direction dp1 as the rotation axis, is referred to as the second reference image 32 in the present embodiment. The second reference image 32 and the first reference image 31 are orthogonal to each other. The second reference image 32 is also orthogonal to the third reference image 33 being parallel to the ultrasound emitting surface 28 that is described below (see (b-3) in FIG. 3(b)).

In addition, an image extracted from the cross section that is parallel to the ultrasound emitting surface 28 is referred to as the third reference image 33 in the present embodiment. The third reference image 33 is orthogonal to each of the first reference image 31 and the second reference image 32 (see (b-3) in FIG. 3(b)).

Figure 11:
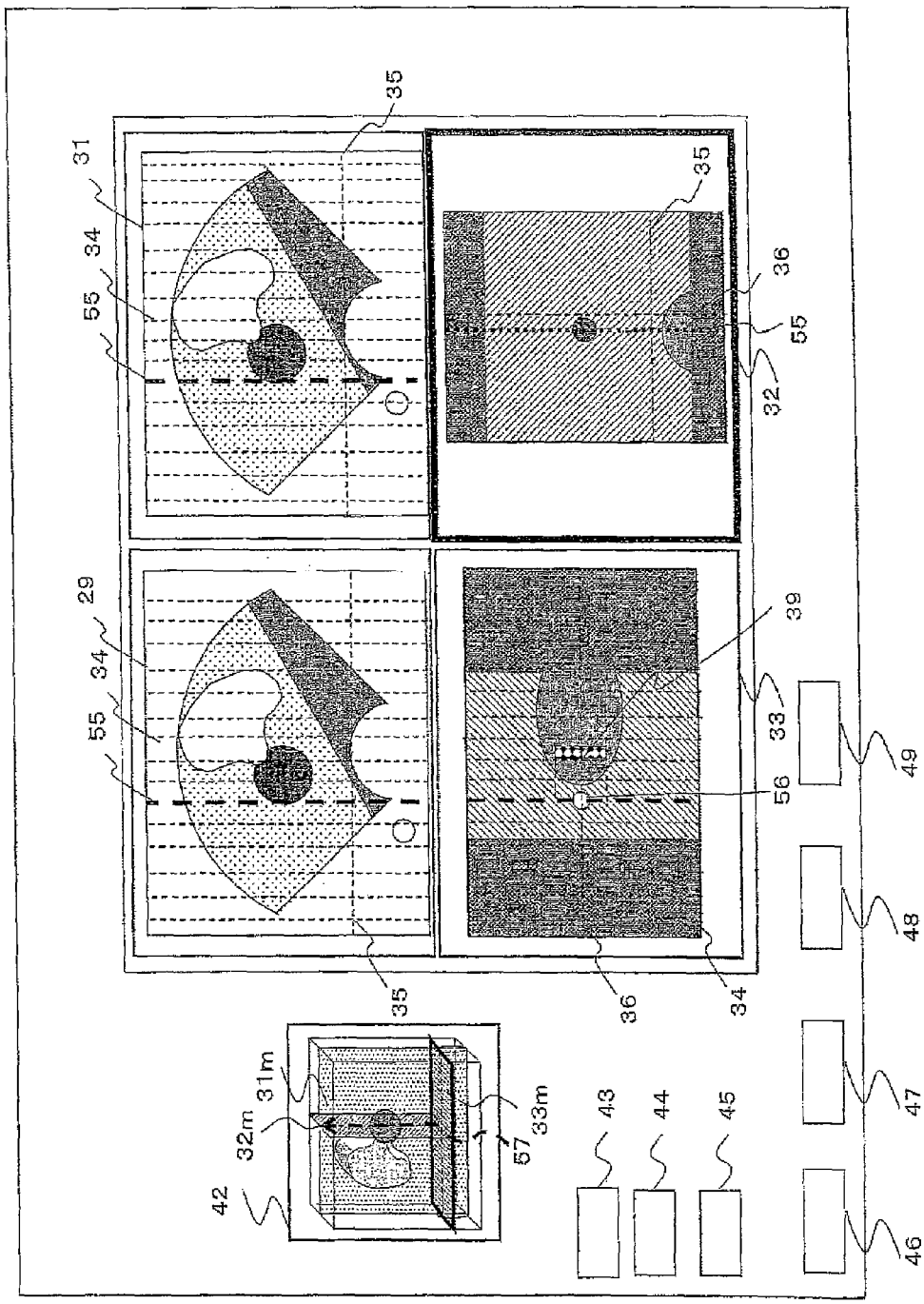
FIG. 11 illustrates one example of the display screen relating to the second embodiment, showing the display example when the ultrasound probe C in FIG. 2 is employed.
Figure 12:
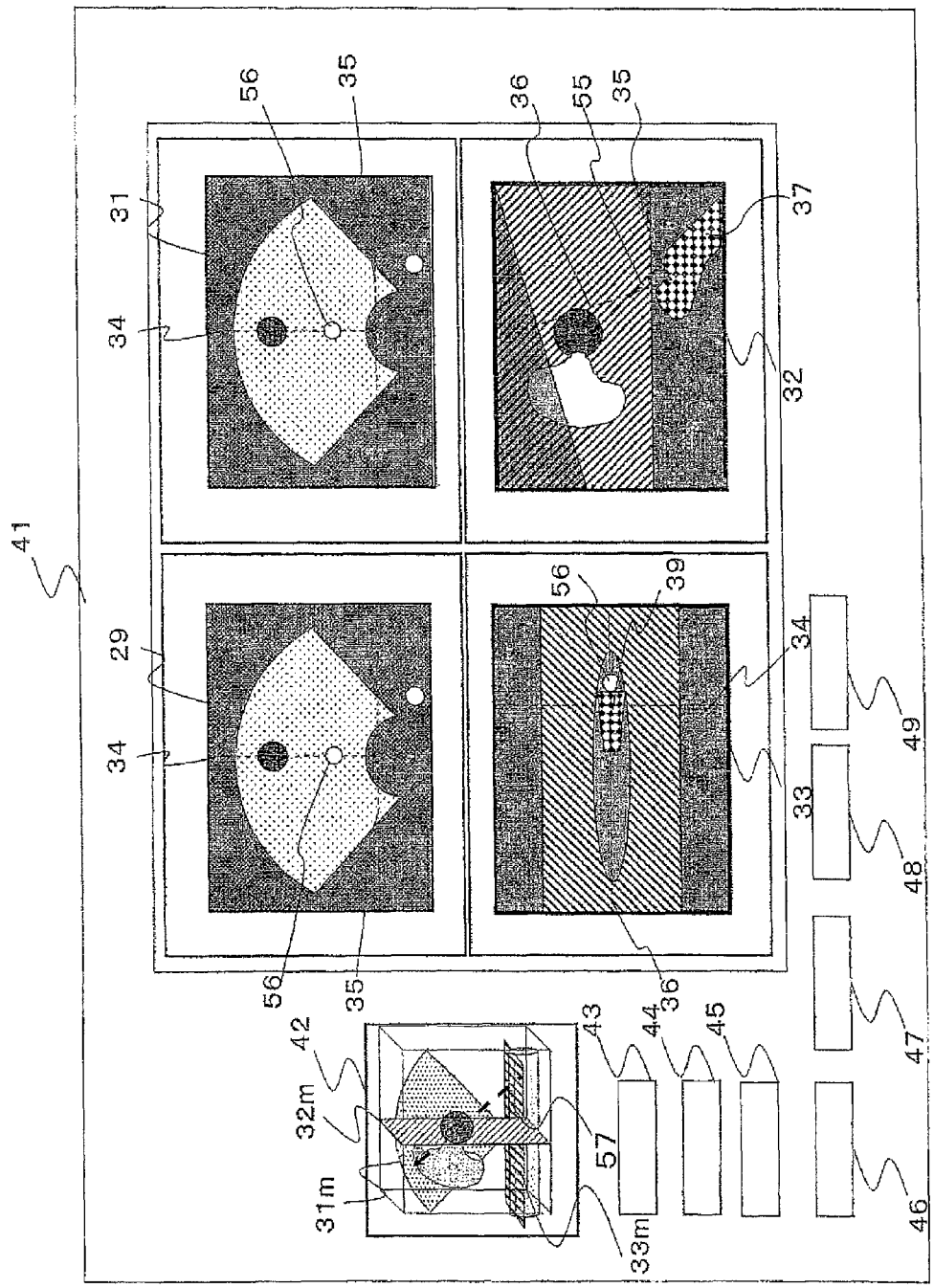
FIG. 12 illustrates one example of the display screen relating to the second embodiment, showing the display example when the ultrasound emitting surface 21 of the ultrasound probe A in FIG. 2 is employed.

It is to be noted that in the figures from FIG. 3 to FIG. 7, the ultrasound image 29 and the FOV of the first reference image 31, and the mark 31m indicating the position of the first reference image 31 in the guide image, which will be described below, are depicted in black dots on a white background. The region of white dots in a black background indicates a region within the FOV, obtained by imaging the intestine of the test object. The FOV of the second reference image 32, and the mark 32m indicating the position of the second reference image 32 in the guide image, which will be described below, are depicted in hatching with falling diagonal strokes from top left to bottom right, and the FOV of the third reference image 33, and the mark 33m indicating the position of the cross section 33 in the guide image, which will be described below, are depicted in hatching with falling diagonal strokes from top right to bottom left. In addition, the outside FOV is depicted using grid-like hatching with the following diagonal strokes; from top left to bottom right and from top right to bottom left. A white dot in the outside FOV of the ultrasound image 29 and the first reference image represents a mark (orientation mark) indicating the viewpoint position of the ultrasound 29 and the first reference image. FIG. 11 and FIG. 12 used for explaining the second embodiment are similarly illustrated.

The reference image generator 12 has a function for extracting the FOV (or the outside FOV) of the ultrasound image 29 obtained by the ultrasound probe 2 and reducing the brightness of a region that corresponds to the outside FOV in each of the reference images (the first reference image 31, the second reference image 32, and the third reference image 33). In addition, the reference image generator 12 has a function for hiding a region corresponding to the outside FOV in each of the reference images (the first reference image 31, the second reference image 32, and the third reference image 33). The reference images (the first reference image 31, the second reference image 32, and the third reference image 33) are orthogonal to one another.

In other words, the reference image generating means (the reference image generator 12) has a function for extracting the FOV of the ultrasound image, and reducing the brightness of the region corresponding to the outside FOV in each of the reference images being orthogonal to one another. In addition, the reference image generating means (the reference image generator 12) has a function for extracting the FOV of the ultrasound image, and hiding the region corresponding to the outside FOV in each of the reference images being orthogonal to one another.

It is further possible to select, according to the settings by the operator, displaying or hiding the reference image portion that corresponds to the outside FOV of each reference images (the first reference image 31, the second reference image 32, and the third reference image 33). Those functions above may bring clarity to the correspondence relationship between the ultrasound image and each of the reference images (the first reference image 31, the second reference image 32, and the third reference image 33), thereby allowing the operator to easily grasp the correspondence relationship between both images.

The image as shown in (b-4) in FIG. 3(*b*) is the first reference image 31 that is generated by extracting from the three-dimensional volume data 30. The dotted line 34 within the first reference image 31 indicates the position of the second reference image 32, and the dotted line 35 indicates the position of the third reference image 33. This configuration facilitates grasping the positional relationship between the first reference image 31 being displayed, and the second and third reference images. Furthermore, also in the ultrasound image 29, the dotted lines 34 and 35 indicating the positions of the second reference image 32 and the third reference image 33 are displayed, respectively.

The image shown in (b-5) in FIG. 3(*b*) is the second reference image 32 being generated after extracted from the three-dimensional volume data 30. An illustration 37 indicating the position of the ultrasound probe 2 is displayed in a superimposed manner on the second reference image 32. The illustration 37 has a region 37*r* indicating the shape of the cross section of the ultrasound probe 2 in the second reference image 32 and the dotted line 37*l* indicating the outline of the ultrasound probe 2 viewed from the second reference image 32. In other words, the dotted line 37*l* is an outline obtained by projecting the ultrasound probe 2 in parallel on the second reference image 32. That is, the ultrasound probe mark is displayed by using the outline indicating the shape of the ultrasound probe 2 that is obtained by projecting the ultrasound probe 2 on the cross section of the reference image. The ultrasound probe mark is displayed by using an area which represents the shape of the cross section of the ultrasound probe 2.

Therefore, if the ultrasound emitting surface 28 of the ultrasound probe 2 exists within the second reference image 32, a rectangle region 37*r* (the outline thereof corresponds to the dotted line 37*l*) is depicted within the illustration 37, and if it does not exist in the second reference image 32, only the outline 37*l* is delineated without the rectangle region 37*r* in the illustration 37. In the case of the second reference image 32 in FIG. 3, since a part of the ultrasound emitting surface 28 of the ultrasound probe 2 is included in the second reference image 32, the illustration 37 including the rectangle region 37*r* is depicted.

Furthermore, in the second reference image 32, there is displayed the outside FOV 38 that is displayed on the first reference image 31. The outside FOV 38 is displayed with reduced brightness relative to the FOV. In addition, there are displayed the dotted line 36 indicating the position of the first reference image 31, and the dotted line 35 indicating the position of the third reference image 33 in superimposed manner on the second reference image 32.

The image in (b-6) of FIG. 3(*b*) is the third reference image 33 that is generated after being extracted from the three-dimensional volume data 30. An illustration 39 indicating the position of the ultrasound probe 2 is displayed in a superimposed manner on the third reference image 33. The illustration 39 has a region 39*r* indicating the shape of the cross section of the ultrasound probe 2 in the third reference image 33 and has the dotted line 39*l* indicating the outline of the ultrasound probe 2, viewed from the third reference image 33. In other words, the dotted line 39*l* is an outline obtained by projecting the ultrasound probe 2 in parallel on the third reference image 33.

Therefore, if the ultrasound emitting surface 28 of the ultrasound probe 2 exists within the third reference image 33, a rectangle region 39*r* is depicted within the illustration 39, and if it does not exist in the third reference image 33, only the outline 39*l* is delineated without the rectangle region 39*r* in the illustration 39. In the case of the third reference image 33 in FIG. 3, since a part of the ultrasound emitting surface 28 of the ultrasound probe 2 is included in the third reference image 33, the illustration 39 including the rectangle region 39*r* is depicted.

Furthermore, in the third reference image 33, there is displayed the outside FOV 40 that is displayed on the first reference image 31. The outside FOV 40 is displayed with reduced brightness relative to the FOV. The dotted line 36 indicating the position of the first reference image 31 and the dotted line 34 indicating the position of the second reference image 32 are displayed in a superimposed manner on the third reference image 33.

The aforementioned dotted lines 34 to 36 may be configured, for example, in such a manner that the color of the dotted line is changed for each cross section, or the dotted lines may be differentiated by display formats of various dotted line types, such as a dot-and-dash line, a chain double-dashed line, and a broken line, or both the color of the dotted line and the types thereof may be used to differentiate the dotted lines for the respective reference images. If the reference images are differentiated by the color of the dotted line, in order to clarify the correspondence relationship between the dotted line and the reference image being associated, the display region of the reference image may be bordered with the color of the dotted line being associated, or an image identification mark with the same color or the same display format may be attached. It is the reference image generator 12 that executes the process for displaying the dotted lines 34 to 36 in such a manner as superimposed on the reference image. In the present embodiment, in the illustrations 37 and 39 representing the ultrasound probe 2, both the rectangle regions 37r and 39r, and the outlines 37l and 39l are used together, but only either one of them may be used.

Next, based on the figures from FIG. 4 to FIG. 9, a display screen of the first embodiment will be explained.

As shown in FIG. 4, on the screen 41 relating to the present embodiment, there are displayed the ultrasound image 29, the first reference image 31 made up of the same cross section as that of the ultrasound image 29, the second reference image 32 obtained by rotating the first reference image 34 by 90° or by 270°, and the third reference image 33 being parallel to the ultrasound emitting surface, and the guide image 42. Furthermore, the screen 41 is provided with soft buttons allowing various functions to be executed. Those soft buttons include an ON/OFF switching button 43 for the guideline on the ultrasound image, an ON/OFF switching button 44 for the guideline on the reference image, an ON/OFF switching button 45 for displaying the illustration indicating the position of the ultrasound probe on the reference image, an ON/OFF switching button 46 for a navigation function, an image selection button 47 for selecting either of the second reference image and the third reference image as an image to be moved or rotated, a moving direction (backward and forward directions/optional direction within the same plane) switching button 48, and the rotating direction (backward and forward direction, left and right/vertical direction) switching button 49.

The guide image 42 is obtained by applying volume rendering, for instance, based on the three-dimensional volume data of the test object imaged by an MRI device or a CT scanner, and displaying the mark 31m indicating the position of the first reference image, the mark 32m indicating the position of the second reference image, and the mark 33m indicating the position of the third reference image, in a superimposing manner on the three-dimensionally visualized image that visualizes the three-dimensional internal structure of the test object.

When the operator presses the ON/OFF switching button 43 for the guideline on the ultrasound image, it is possible to select displaying/hiding the dotted lines 34 and 35 being associated on the ultrasound screen. It is to be noted that the image processor 14 performs the processing for displaying the dotted lines 34 and 35 in a superimposed manner on the ultrasound image 29.

When the operator presses the ON/OFF switching button 44 for the guideline on the reference image, it is possible to select displaying/hiding the dotted lines 34, 35, and 36 indicating the positions of other reference images being displayed in a superimposed manner, on the first reference image 31, the second reference image 32, and the third reference image 33.

When the operator presses the ON/OFF switching button 45 for the displayed illustration indicating the position of the ultrasound probe, it is possible to select displaying/hiding the illustrations 37 and 39 indicating the position of the ultrasound probe being displayed in a superimposed manner on the second reference image 32 and the third reference image 33.

When the operator presses the ON/OFF switching button 46 for the navigation function, switching takes place to a navigation mode, and the second reference image 32 or the third reference image 33 being set as a default in advance is highlighted. Functions of the navigation mode will be described in detail in the following.

When the operator presses the image selection button 47, it is possible to select either of the second reference image 32 and the third reference image 33. As a method for selecting an image, it is possible to use the image selection button on the console of the ultrasound diagnostic device 10 not illustrated, in addition to the image selection button 47 made up of the screen buttons mounted on the monitor 15. It is further possible that after pressing the pointer display button on the console of the ultrasound diagnostic device 10 not illustrated, and displaying the pointer on the monitor 15, the second reference image 32 or the third reference image 33 is selected directly by the pointer.

Alternatively, before entering the navigation mode, an image to be selected upon entering the navigation mode may be set as a default in advance by the image selection button 47.

When the operator presses the moving direction switching button 48, it is possible to select from the following; moving the selected image (corresponding to the third reference image 33 in the screen 41) along the backward and forward directions on the paper of FIG. 4, or moving the selected image in an optional direction within the same plane.

When the operator presses the rotating direction switching button 49, it is possible to select from the following; rotating the selected image (corresponding to the third reference image 33 in the screen 41) assuming the right-and-left direction on the paper of FIG. 4 as the rotating axis, and rotating the selected image assuming the vertical direction on the paper of FIG. 4 as the rotating axis.

In the aforementioned navigation mode, the reference image being set as the default is highlighted, and there are some other displays being highlighted along therewith. Hereinafter, an explanation will be made taking an example that the second reference image 32 is set as the default.

In the state where the second reference image 32 is selected as the default image, the image selection button 47 is pressed and it is possible to select the third reference image 33 as the image to be used in the navigation mode. The highlighted display according to the navigation mode may be implemented by using a display mode that is different depending on whether it is highlighted or not, such as bordering the image with a colored line or a bold line, for instance. The screen 41 illustrates the state that the third reference image 33 is highlighted by displaying the display outline 50 in a superimposed manner and highlighting of the second reference image 32 is released.

In the navigation mode, the dotted line 35 is highlighted, indicating the display position of the highlighted reference image, i.e., the third reference image, the dotted line 35 being displayed on the ultrasound image 29 and on the non-highlighted reference images, i.e., the first reference image 31 and the second reference image 32.

Furthermore, the mark 33m is also displayed in a highlighted manner on the guide image 42, indicating the position of the reference image being highlighted, i.e., the third reference image 33.

Further in the navigation mode, the dotted line 35 is displayed, indicating the current display position of the highlighted reference image (i.e., the third reference image 33 in the screen 41), in the non-highlighted images (i.e., the ultrasound image 29, the first reference image 31, and the second reference image 32 in the screen 41). The dotted line 35 is constantly displayed, while moving sequentially as the dotted line 35A, 35B, 35C, and more, or 35a, 35b, 35c, and more, in accordance with the moving pitch of the third reference image 33. It is to be noted that as for the suffix of the dotted line 35, the uppercase suffix is used for delineating the position in the depth direction, away from the current position to a deeper position in the order of A, B, and C, and more, and the lowercase suffix is used for delineating the position, away from the current position to a shallower position in the order of a, b, c, and more.

In the state of FIG. 4, after the moving direction switching button 48 is pressed and the backward/forward direction is selected as the moving direction, the track ball 16*t* on the ultrasound diagnostic device 10 is rotated upwardly as shown in FIG. 5(*a*) (a-1), or a pointing device not illustrated, for instance, a mouse wheel of a mouse being connectable to the ultrasound diagnostic device 10, is rotated upwardly, the third reference image 33 moves in the deeper direction along the depth direction of ultrasound wave (the direction away from the ultrasound probe 2, that is, the direction of arrow B in FIG. 5(*b*) (b-5)).

Accordingly, the third reference image 33 in FIG. 5(*a*)(a-2) is switched from 33A, 33B, 33C, and more, as shown in FIG. 5(*a*)(a-3), and the highlighted dotted line 35 being displayed on the ultrasound image 29, the first reference image 31, and the second reference image 32, moves sequentially from 35A, 35B, 35C, and more in this order. On this occasion, in the illustration 39 indicating the position of the ultrasound probe 2 that is displayed in the third reference image 33, the rectangle region 39*r* becomes smaller gradually and it is changed to a display in which only the dotted line 39*l* remains, while the third reference image moves to a deeper direction along the depth direction dp1. In addition, when the third reference image 33 as shown in FIG. 5(*b*) (b-3) moves in deeper direction along the depth direction dp1, and makes a transition to the third reference image 33C in FIG. 5(*b*)(b-4), the mark 33*m* of the cross section displayed in the guide image 42 also moves along the depth direction dp1 (it moves from the mark 33*m* in FIG. 5(*b*)(b-1) to the mark 33*m*C in FIG. 5(*b*)(b-2)).

On the other hand, in the state as shown in FIG. 4, after the moving direction switching button 48 is pressed and the backward/forward direction is selected as the moving direction, the track ball 16*t* on the ultrasound diagnostic device 10 is rotated downwardly as shown in FIG. 6(*a*) (a-1), or a pointing device not illustrated, for instance, a mouse wheel of a mouse being connectable to the ultrasound diagnostic device 10 is rotated downwardly, the third reference image 33 moves in the shallower direction along the depth direction dp1 of the ultrasound wave (the direction coming closer to the ultrasound probe 2, that is, the direction of arrow C).

Therefore, the third reference image 33 as shown in FIG. 6(*a*)(a-2) is switched to 33*a*, 33*b*, 33*c*, and more in this order, as shown in FIG. 6(*a*)(a-3), and the highlighted dotted line 35 displayed on the ultrasound image 29, the first reference image 31, and the second reference image 32 moves sequentially 35*a*, 35*b*, 35*c*, and more in this order. On this occasion, in the illustration 39 indicating the position of the ultrasound probe 2 that is displayed in the third reference image 33, as the third reference image 33 moves toward the shallower position along the depth direction dp1, the area of the rectangle region 39*r* representing a part included in the third reference image 33 is displayed in such a manner as becoming larger gradually.

When the third reference image 33 as shown in FIG. 6(*b*) (b-3) moves along the depth direction dp1 and makes a transition to the third reference image 33*c* as shown in FIG. 6(*b*) (b-4), the mark 33*m* indicating the position of the third reference image 33 that is displayed in the guide image 42 also moves along the depth direction dp1 (it moves from the mark 33*m* in FIG. 6(*b*) (b-1) to the mark 33*mc* in FIG. 6(*b*) (b-2)).

Next, with reference to FIG. 7, the processing for moving the second reference image 32 will be explained. In the state where the second reference image 32 is selected, after the backward-and-forward direction is selected as the moving direction by the moving direction switching button 48, the track ball 16*t* is rotated in the right direction as shown in FIG. 7(*a*) (a-1). Then, the second reference image 32 moves from the base position along the direction of arrow D in the ultrasound volume data 30 as shown in FIG. 7(*b*) (b-3) and makes a transition to the second reference image 32C as shown in FIG. 7(*b*) (b-4). In other words, in the positional relationship with the ultrasound probe 2, as shown in FIG. 7(*b*) (b-5), the base position is at the center axis of the ultrasound wave emitted from the ultrasound probe 2, and the position moves along the direction of arrow D with the rotation of the track ball 16*t*, and makes a transition to the second reference image 32C. Accordingly, the mark 32*m* indicating the position in the guide image 42 as shown in FIG. 7(*b*) (b-1) makes a transition to the mark 32*m*C as shown in FIG. 7(*b*) (b-2).

In addition, along with the rotation of the track ball 16*t* in the right direction, the second reference image 32 as shown in FIG. 7(*a*) (a-2) is switched to 32A, 32B, 32C, and more, in this order as shown in FIG. 7(*a*) (a-3), and the dotted line 34 displayed on the ultrasound image 29, the first reference image 31, and the third reference image 33 moves sequentially to 34A, 34B, 34C, and more, in this order. On this occasion, as for the illustration 37 indicating the position of the ultrasound probe 2 that is displayed in the second reference image 32, every time when the display cross section of the second reference image 32 is switched, the rectangle region 37*r* becomes smaller gradually, and then, only the dotted line 37*l* is displayed, eventually. This is because, the field of view is updated every time when the cross section of the second reference image 32 is switched, and thus the positional relationship between the ultrasound probe 2 and the second reference image 32 is changed.

Next, with reference to FIG. 8, movement of images within the ultrasound emitting plane will be explained. As shown in FIG. 8, it is assumed that in the initial state as shown in FIG. 8 (*a*) (a-1), there are displayed on the monitor 15, the ultrasound image 29, the first reference image 31, the second reference image 32, and the third reference image 33 at the base position. On the ultrasound image 29, the first reference image 31, and the second reference image 32, there is displayed the dotted line 35 indicating the position of the third reference image 33.

Here, after selecting "the same plane" as the moving direction by the moving direction selection button 48 and the trackball 16*t* is rotated in the right direction, the third reference image 33 makes a transition from the base position to the third reference image 33R within the ultrasound volume data 30 (see FIG. 8(*b*)). As a result, on the monitor 15, the third reference image 33R is updated and displayed (see FIG. 8(*a*) (a-2)). It is to be noted that even though the third reference image 33 moves to the third reference image 33R, the position of the dotted line 35 indicating the third reference image 33 on the ultrasound image 29, the first reference image 31, and the second reference image 32 is not changed, and thus those images are not changed.

As shown in FIG. 9(*a*), when the track ball 16*t* is manipulated to rotate in each of the directions a1 to a8, the cross-section position for extracting the third reference image 33 moves according to the rotation direction and rotating amount of the track ball 16*t*. In FIG. 9(*a*), when the track ball 16*t* is rotated in each of the rotating directions a1, a2, a3, a4, a5, a6, a7, and a8, the third reference image 33 makes a transition, as shown in FIG. 9(b), from the third reference image 33 to each third reference image 33Front, 33FrontR, 33R, 33BackR, 33Back, 33BackL, 33L, and 33FrontL. In the images after the transition, there is displayed the mark 39 indicating the position of the moved ultrasound probe.

The directions a1 and a5 indicate the movement along the depth direction. In the case where the image moves along the direction a1, the dotted line 35 being displayed in a superimposed manner on the ultrasound image 29, the first reference image 31, and the second reference image 32, moves to 35A, 35B, and 35C, for instance, as shown in FIG. 8(a) (a-2).

The directions a3 and a7 indicate the movement along the direction orthogonal to the depth direction, within the ultrasound emitting plane. On this occasion, since the position of the third reference image 33 in the depth direction does not change, the position of the dotted line 35 indicating the third reference image on the ultrasound image 29, the first reference image 31, and the second reference image 32 does not change, either.

The directions a2 and a8 indicate the movement combining the movement in a deeper direction along the depth direction, and the right or left movement along the direction orthogonal to the depth direction. On this occasion, the position of the dotted line 35 indicating the third reference image 33 on the ultrasound image 29, the first reference image 31, and the second reference image 32, is changed by the moving amount corresponding to the movement along the depth direction of the third reference image 33.

The directions a4 and a6 indicate the movement combining the movement in a shallower direction in the depth direction, and the right or left movement along the direction orthogonal to the depth direction. On this occasion, the position of the dotted line 35 indicating the third reference image 33 on the ultrasound image 29, the first reference image 31, and the second reference image 32, is changed by the moving amount corresponding to the movement along the depth direction of the third reference image 33.

Next, with reference to FIG. 10, an explanation will be made as to the rotation movement. As shown in FIG. 10, in the state where the second reference image 32 is selected by the image selection button 47, and the rotating direction is set to be the "backward, forward, left, right", when the track ball 16t is rotated upwardly, the second reference image 32 at the base position (see FIG. 10(a) (a-1)) is rotated in the backward direction with respect to the monitor 15, assuming the left-right direction of the second reference image 32 as the rotation axis Ax2 (see FIG. 10(a) (a-2)), and the second reference image 32 makes a transition to the second reference image 32s3 (see FIG. 10(b)).

Similarly, when the track ball 16t is rotated downwardly, the second reference image 32 is rotated in the forward direction with respect to the monitor 15, assuming Ax2 as the rotation axis (see FIG. 10(a) (a-3)), and the second reference image 32 makes a transit to the second reference image 32s4 (see FIG. 10(b)).

When the track ball 16t is rotated in the left direction, assuming the backward and forward direction of the second reference image 32 as the rotation axis Ax1, the second reference image 32 is rotated to the left (see FIG. 10(a) (a-5)), and it makes a transition to the second reference image 32s2 (see FIG. 10(b)). Similarly, when the track ball 16t is rotated in the right direction, assuming the backward and forward direction of the second reference image 32 as the rotation axis Ax1, the second reference image 32 is rotated to the right (see FIG. 10(a) (a-4)), and the second reference image 32 makes a transition to the second reference image 32s1 (see FIG. 10(b)).

With the rotation as described above, the mark 32m indicating the position of the second reference image 32 that is displayed on the guide image 42 is also rotated, following the movement of the trackball 16t.

According to the present embodiment, there are provided an ultrasound probe 2 for emitting an ultrasound wave and receiving a reflected wave of the ultrasound wave, a first position detecting means (position sensor 4) for detecting the position of the ultrasound probe 2, an ultrasound image generating means (ultrasound image generator 6) for generating an ultrasound image by using a reflected echo signal based on the reflected wave, a reference image generating means (reference image generator 12) for generating a reference image of an arbitrary cross section by using three-dimensional volume data of a test object and displaying an ultrasound probe mark indicating the position of the ultrasound probe in a superimposing manner on the reference image, and a display means (monitor 15) for displaying the ultrasound image and the reference image.

There is provided an ultrasound image display method including a step of generating a reference image of an arbitrary cross section by using the three-dimensional volume data of the test object, a step of displaying an ultrasound probe mark indicating the position of the ultrasound probe 2 in a superimposed manner on the reference image, and a step of displaying an ultrasound image based on a reflected wave received from the ultrasound probe 2 and the reference image. Therefore, the mark indicating the position of the ultrasound probe 2 that is displayed on the reference image facilitates grasping the positional relationship between the reference image and the ultrasound probe 2.

Particularly, in the case of the ultrasound probe to be inserted in a body cavity, the position of the ultrasound probe is invisible. Therefore, facilitating a grasp of the positional relationship with the reference image may contribute to enhancement of diagnostic performance.

In addition, a mark indicating the position of each reference image is displayed on another reference image, the ultrasound image, and the guide image, thereby facilitating a grasp of mutual positional relationship among those images, and contributing to further enhancement of diagnostic performance.

Second Embodiment

In the second embodiment, upon performing a puncture, an entry pathway of a puncture needle is displayed together. Hereinafter, with reference to FIG. 11 and FIG. 12, the second embodiment will be explained. FIG. 11 illustrates one example of the display screen relating to the second embodiment, showing a display example when the ultrasound probe C in FIG. 2 is employed. FIG. 12 illustrates a display example illustrating an example of the display screen relating to the second embodiment when the ultrasound emitting surface 21 of the ultrasound probe A in FIG. 2 is employed.

When displaying relating to the present embodiment is carried out, an operator presses a "puncture guide" button on the console of an ultrasound diagnostic device not illustrated. In response thereto, the pathway calculator 53 calculates the entry pathway of the puncture needle 51, based on a shape of the ultrasound probe connected to the ultrasound diagnostic device and information of physical position of the puncture needle 51 going in and out, assuming an extension of the core line of the puncture needle 51 as the pathway of the puncture needle 51, and outputs data indicating the pathway, to the reference image generator 12, the guide image generator 13, and the image processor 14. The reference image generator 12 displays the pathway of the puncture needle 51 in a superimposed manner on each reference image, the guide image generator 13 displays the pathway of the puncture needle 51 in a superimposed manner on the guide image 42, and image processor 14 displays the pathway of the puncture needle 51 in a superimposed manner on the ultrasound image 29. Alternatively, the puncture needle 51 used in the present embodiment is provided with a position sensor 52, and the pathway calculator 53 may have a function for calculating the present position and inclination of the puncture needle 51 based on the outputs from the source origin 5 and the position sensor 52, calculating the extension of the core line of the puncture needle 51 as the pathway of the puncture needle 51, and displaying the pathway in a superimposed manner.

As shown in FIG. 11, a puncture guideline (hereinafter, abbreviated as "guideline") 55 is displayed, indicating the entry pathway of the puncture needle 51 that is used upon performing a puncture. On this occasion, there is displayed the guideline 55 on the first reference image 31, at the same position and in the same size as the guideline 55 displayed on the ultrasound image 29. The guideline 55 is displayed in a superimposed manner on the second reference image 32. A guideline mark 56 is displayed at the position where the puncture needle 51 passes through, in a superimposed manner on the third reference image 33.

On the guide image 42, there is displayed an arrow 57, indicating the position of the guideline 55. If the position of the guideline 55 displayed on the first reference image 31 is verified on the second and third reference images 32 and 33, the navigation function ON/OFF switching button 46 is pressed to establish the navigation mode.

Next, under the condition that the image selection button 47 is pressed to select the second reference image 32 or the third reference image 33, the track ball 16t is rotated to display the cross section where the guideline 55 is displayed, and then, the position of the guideline 55 is verified. It is further possible to configure the switching to the navigation mode in such a manner that the switching is performed automatically at the time when the "puncture guide" button is pressed. FIG. 11 illustrates the example where the position of the guideline 55 is verified on the second reference image 32, and the guideline 55 is displayed at the center of the second reference image 32 and along the vertical direction of the display screen.

It is further possible to verify the path along which the guideline 55 goes through on the third reference image 33, in other words, the position of the guideline mark 56. On this occasion, the image selection button 47 is pressed to perform switching to select the third reference image 33 and the track ball is rotated, thereby displaying a cross section where the guideline mark 56 is displayed. Accordingly, it is possible to verify the position of the guideline mark 56 on the third reference image 33.

Next, with reference to FIG. 12, an explanation will be made as to the case where the ultrasound probe A in FIG. 2 is employed. As shown in FIG. 2, the ultrasound probe A is equipped with the ultrasound emitting surfaces 20 and 21, and in the following explanation, the ultrasound emitting surface 21 is taken as an example. The same explanation is applied to the case where the ultrasound emitting surface 20 or the ultrasound probe B in FIG. 2 is employed.

As shown in FIG. 12, when the ultrasound probe A is employed, there is a characteristic that the depth direction of the ultrasound emitting surface 21 is inclined with respect to the traveling direction of the ultrasound probe A, and thus the guideline 55 is drawn in an oblique direction.

Therefore, on the ultrasound image 29, the first reference image 31, and the third reference image 33, the guideline mark 56 is displayed at the position where the puncture needle 51 passes through, in a superimposed manner on the ultrasound image 29, the first reference image 31, and the third reference image 33, and the guideline 55 indicating the entry pathway of the puncture needle 51 is displayed on the second reference image 32. On this occasion, the mark 37 indicating the position of the ultrasound probe 2 that is displayed on the second reference image 32 and the mark 39 indicating the position of the ultrasound probe 2 that is displayed on the third reference image 33 are displayed in such a manner as being adjusted to the shape of the cross section of the ultrasound probe B in each reference image. The position of each of the guideline 55 and the guideline mark 56 is verified using the track ball after establishing the navigation mode, similar to the case of the ultrasound probe C.

According to the present embodiment, a second position detecting means (a position sensor 52) for detecting the position and posture of the puncture needle 51 for puncturing the test object, and a pathway calculating means (the pathway calculator 53) for calculating the position of the core line of the puncture needle 51 based on the detected position and posture of the puncture needle 51 are provided, and the reference image generating means (the reference image generator 12) displays the mark indicating the extension of the core line of the puncture needle 51 being calculated, in a superimposed manner on the reference image. The reference image generating means (the reference image generator 12) generates the reference image that includes the extension of the core line of the puncture needle 51, and that is made up of a cross section being parallel to the extension.

There are also provided the second position detecting means (the position sensor 52) for detecting the position and posture of the puncture needle 51 for puncturing the test object, the pathway calculating means for calculating the position of the extension of the core line of the puncture needle 51 based on the detected position and posture of the puncture needle 51, and a second image processing means (an image processor 14) for displaying the mark indicating the extension of the core line of the puncture needle 51 being calculated, in a superimposed manner on the ultrasound image.

This facilitates grasping the mutual positional relationship among the first, second, third reference images 31, 32, and 33, and the position through which the puncture needle 51 passes. Particularly, in the case where a puncture using the ultrasound probe 2 is performed within the body cavity of the test object, though the position of the ultrasound probe 2 is invisible, it becomes possible to verify a portion through which the puncture needle 51 passes on the first, second, and third reference images 31, 32, and 33, the ultrasound image 29, and the guide image 42, thereby allowing a safer puncturing. In addition, it is possible to display the position of the ultrasound probe, thereby allowing verification of the entry pathway of the puncture needle, with respect to the current position of the ultrasound probe.

EXPLANATION OF REFERENCES 1 ultrasound diagnostic device main body, 2 ultrasound probe, 3 position sensor fixation mechanism, 4 position sensor, 5 source origin, 6 ultrasound image generator, 7 cine memory, 8 ultrasound volume data generator, 9 volume data recorder, 10 ultrasound diagnostic device, 11 scan plane acquisition part, 12 reference image generator, 13 guide image generator, 14 image processor, 15 monitor, 16 movement/rotation amount input part, 17 medical diagnostic imaging device, 51 puncture needle, 52 position sensor, 53 pathway calculator

What is claimed is:

1. An ultrasound diagnostic device comprising,
   an ultrasound probe which emits an ultrasound wave and receives a reflected wave of the ultrasound wave,
   a first position detector which detects a position of the ultrasound probe,
   an ultrasound image generator which generates an ultrasound image by using a reflected echo signal based on the reflected wave,
   a reference image generator which generates plural reference images of an arbitrary cross section by using three-dimensional volume data of a test object and displays an ultrasound probe mark indicating the position of the ultrasound probe in a superimposed manner on the reference image, and
   an image processor which displays the ultrasound image and the reference image on a display,
   wherein the reference image generator:
      indicates a position of another reference image by displaying a line on each of the plural reference images, and
      draws an area representing a shape of the ultrasound probe when an ultrasound emitting plane of the ultrasound probe exists within a reference image of the plural reference images, and draws only an outline of the probe when the ultrasound emitting plane of the ultrasound probe does not exist within the reference image.

2. The ultrasound diagnostic device according to claim 1, further comprising,
   an ultrasound volume data generator which generates three-dimensional ultrasound volume data of the test object, based on the ultrasound image being more than one, wherein,
   the reference image generator uses the ultrasound volume data being generated to generate the reference image.

3. The ultrasound diagnostic device according to claim 1, wherein,
   the ultrasound probe mark is displayed by using an outline representing a shape that is obtained by projecting the ultrasound probe onto a cross section of the reference image.

4. The ultrasound diagnostic device according to claim 1, wherein,
   the ultrasound probe mark is displayed using an area representing a cross-sectional shape at a cross section of the ultrasound probe.

5. The ultrasound diagnostic device according to claim 1, wherein,
   the reference image generator generates multiple reference images made up of different cross sections, displays on one reference image, a mark indicating a slice pitch of another reference image in a superimposed manner, and highlights the mark indicating the slice pitch of another reference image that is displayed on the display.

6. The ultrasound diagnostic device according to claim 1, further comprising
   a first image processor displays a mark indicating a slice pitch of the reference image in a superimposed manner on the ultrasound image, and highlighting the mark indicating the slice pitch showing a cross-section position of the reference image that is displayed on the display means.

7. The ultrasound diagnostic device according to claim 1, further comprising,
   a second position detector which detects a position and posture of a puncture needle for puncturing the test object, and
   a pathway calculator which calculates a position of an extension of a core line of the puncture needle based on the position and posture of the puncture needle being detected, wherein,
   the reference image generator displays a mark indicating the extension of the core line of the puncture needle being calculated, in a superimposed manner on the reference image.

8. The ultrasound diagnostic device according to claim 7, wherein,
   the reference image generator generates the reference image that includes the extension of the core line of the puncture needle and that is made up of a cross section being parallel to the extension.

9. The ultrasound diagnostic device according to claim 1, further comprising
   a second position detector which detects a position and posture of a puncture needle for puncturing the test object,
   a pathway calculator which calculates a position of an extension of a core line of the puncture needle, based on the position and posture of the puncture needle being detected, and
   a second image processor which displays a mark indicating the extension of the core line of the puncture needle being calculated, in a superimposed manner on the ultrasound image.

10. The ultrasound diagnostic device according to claim 1, wherein,
    the reference image generator has a function for extracting an FOV of the ultrasound image, and reducing brightness of a region corresponding to an outside FOV in each of the reference images being orthogonal to one another.

11. The ultrasound diagnostic device according to claim 1, wherein,
    the reference image generator has a function for extracting an FOV of the ultrasound image, and hiding a region corresponding to an outside FOV in each of the reference images being orthogonal to one another.

12. An ultrasound image display method, comprising,
    a step of generating plural reference images of an arbitrary cross section by using three-dimensional volume data of a test object,
    a step of displaying an ultrasound probe mark indicating a position of an ultrasound probe in a superimposed manner on reference image of the plural reference images, and
    a step of displaying an ultrasound image based on a reflected wave received from the ultrasound probe, and the reference image,
    wherein the step of generating plural reference images further comprises:
       a step of indicating a position of another reference image by displaying a line on each of the plural reference images, a step of drawing a region indicating a shape of the ultrasound probe when an ultrasound emitting plane of the ultrasound probe is included in the reference image, and a step of drawing only an outline of the probe when the ultrasound emitting plane of the ultrasound probe is not included in the reference image.

\* \* \* \* \*